United States Patent
Matsumura et al.

(10) Patent No.: US 11,779,259 B2
(45) Date of Patent: Oct. 10, 2023

(54) COGNITIVE FUNCTION EVALUATION DEVICE, COGNITIVE FUNCTION EVALUATION SYSTEM, COGNITIVE FUNCTION EVALUATION METHOD, AND RECORDING MEDIUM

(71) Applicant: PANASONIC INTELLECTUAL PROPERTY MANAGEMENT CO., LTD., Osaka (JP)

(72) Inventors: Yoshihiro Matsumura, Osaka (JP); Kengo Abe, Nara (JP); Hirobumi Nakajima, Kyoto (JP); Ayumi Kamitani, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 236 days.

(21) Appl. No.: 16/970,106

(22) PCT Filed: Mar. 5, 2019

(86) PCT No.: PCT/JP2019/008632
§ 371 (c)(1),
(2) Date: Aug. 14, 2020

(87) PCT Pub. No.: WO2019/181483
PCT Pub. Date: Sep. 26, 2019

(65) Prior Publication Data
US 2020/0405216 A1     Dec. 31, 2020

(30) Foreign Application Priority Data
Mar. 23, 2018 (JP) ................. 2018-057304

(51) Int. Cl.
*A61B 5/00* (2006.01)
*A61B 5/11* (2006.01)

(52) U.S. Cl.
CPC ............ *A61B 5/4088* (2013.01); *A61B 5/112* (2013.01); *A61B 5/1124* (2013.01); *A61B 5/4023* (2013.01); *A61B 5/486* (2013.01)

(58) Field of Classification Search
CPC ..... A61B 5/4088; A61B 5/112; A61B 5/1124; A61B 5/4023; A61B 5/486; A61B 5/1121;
(Continued)

(56) References Cited

U.S. PATENT DOCUMENTS

| 2008/0281550 | A1* | 11/2008 | Hogle | .......... A61B 5/4023 |
| | | | | 73/865.4 |
| 2012/0101411 | A1* | 4/2012 | Hausdorff | .......... A61B 5/1117 |
| | | | | 600/595 |

(Continued)

FOREIGN PATENT DOCUMENTS

| JP | 2008-173250 A | 7/2008 |
| JP | 2010-178841 A | 8/2010 |

(Continued)

OTHER PUBLICATIONS

International Search Report and Written Opinion dated May 28, 2019 in International Application No. PCT/JP2019/008632; with partial English translation.

(Continued)

*Primary Examiner* — David J. McCrosky
*Assistant Examiner* — Nidhi N Patel
(74) *Attorney, Agent, or Firm* — McDermott Will & Emery LLP

(57) ABSTRACT

A cognitive function evaluation device includes: an obtainment unit configured to obtain, as gait data, at least one of first data and second data, the first data indicating a sway amount of a body of a subject during walking in a first walking section from start of walking of the subject to a
(Continued)

predetermined number of steps, and the second data indicating a sway amount of the body of the subject during walking in a second walking section in a double task state in which the subject is walking while doing a given assignment, the second walking section being after the first walking section; a calculation unit configured to calculate a feature value based on the gait data; an evaluation unit configured to evaluate a cognitive function of the subject, based on the feature value; and an output unit configured to output a result of evaluation by the evaluation unit.

14 Claims, 22 Drawing Sheets

(58) Field of Classification Search
CPC ... A61B 5/1128; A61B 5/6831; A61B 5/7246; A61B 5/7257; A61B 5/7435; A61B 5/0002; A61B 2562/0219; A61B 10/00; G16H 20/70; G16H 20/30; G16H 40/63; G16H 50/30; G16H 50/20
See application file for complete search history.

(56) References Cited

U.S. PATENT DOCUMENTS

| | | |
|---|---|---|
| 2017/0196483 A1 | 7/2017 | Bounyong et al. |
| 2017/0251956 A1 | 9/2017 | Kandori et al. |
| 2019/0290184 A1* | 9/2019 | Matsumura .......... A61B 5/4088 |

FOREIGN PATENT DOCUMENTS

| | | |
|---|---|---|
| JP | 2011-115362 A | 6/2011 |
| JP | 2011-177278 A | 9/2011 |
| JP | 2013-059489 A | 4/2013 |
| JP | 2013-255786 A | 12/2013 |
| JP | 2015-062654 A | 4/2015 |
| JP | 2016-049282 A | 4/2016 |
| JP | 2017-124164 A | 7/2017 |
| JP | 2018-029706 A | 3/2018 |
| WO | 2014/030295 A1 | 2/2014 |

OTHER PUBLICATIONS

Wittwer, J.E., et al., "Timing variability during gait initiation is increased in people with Alzheimer's disease compared to controls.," Dementia and Geriatric Cognitive Disorders., Oct. 8, 2008, vol. 26, No. 3, p. 277-283<DOI:10.1159/000160961>.

Doi, T., et al., "Cognitive function and gait speed under normal and dual-task walking among older adults with mild cognitive impairment," BMC Neurology, Apr. 1, 2014, vol. 14 No. 67, <DOI: 10.1186/1471-2377-14-67>.

Belghali, M., et al., "Loss of gait control assessed by cognitive-motor dual-tasks; pros and cons in detecting people at risk of developing Alzheimer's and Parkinson's diseases.," GeroScience, Jun. 2017, vol. 39, No. 3, p. 305-329, <DOI: 10.1007/s11357-017-9977-7>.

Chinese Office Action with English translation of Search Report dated Jan. 13, 2023 issued in the corresponding Chinese Patent Application No. 201980012817.1.

* cited by examiner

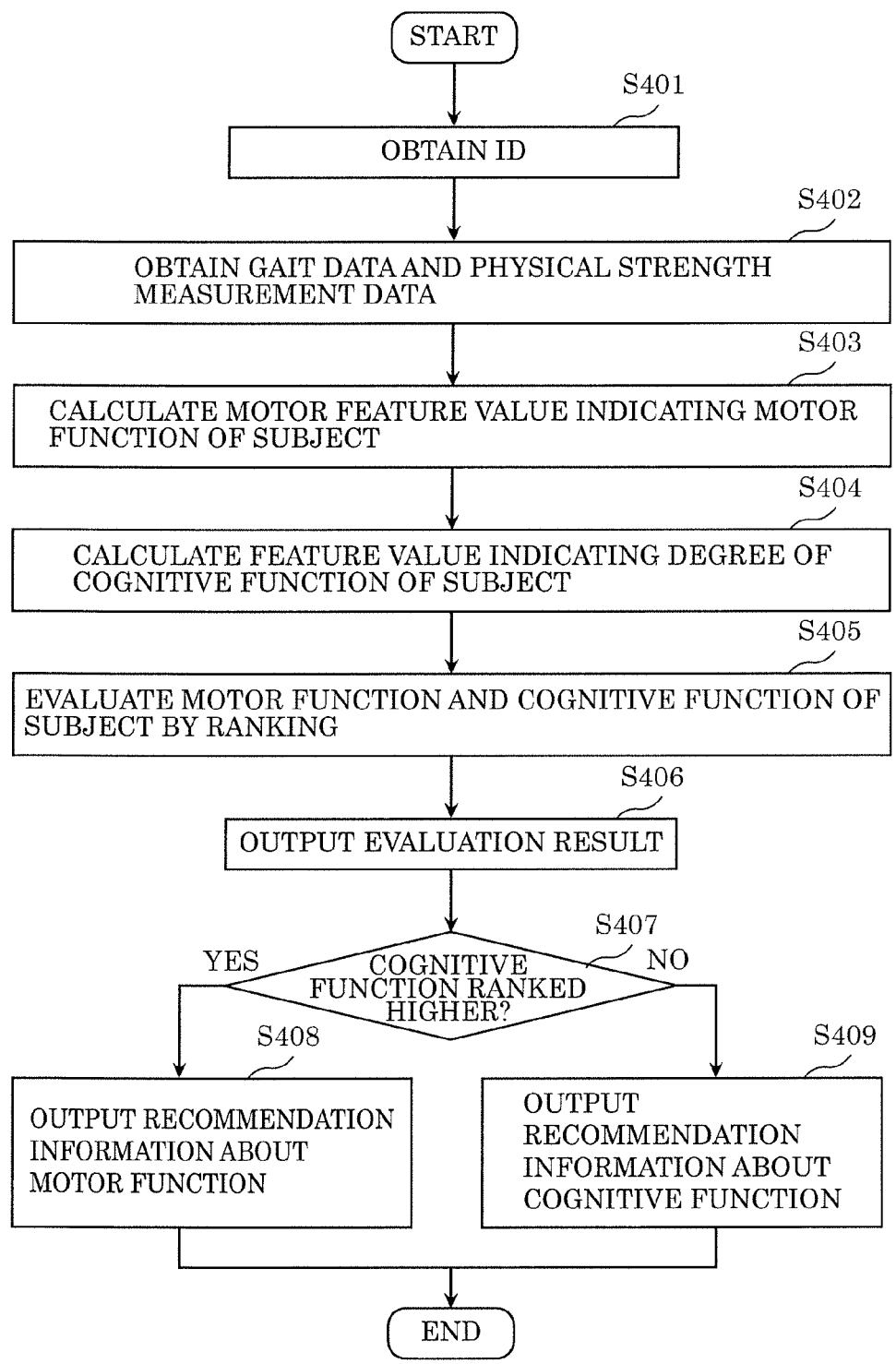

| | | | | | | | |
|---|---|---|---|---|---|---|---|
| ATTRIBUTE INFORMATION | PARAMETER | AGE | GENDER | | | | |
| | SYMBOL | Age | Gend | | | | |
| | MULTIPLE REGRESSION COEFFICIENT | $C_{Age}$ | $C_{Gend}$ | | | | |
| PHYSICAL STRENGTH MEASUREMENT DATA | PARAMETER | GRIP STRENGTH | TIMED UP & GO | STEPPING | 10m WALKING | 5m WALKING | SINGLE-LEG STANDING WITH OPEN EYES | FUNCTIONAL REACH |
| | SYMBOL | Grip | TUG | Step | X10m | X5m | PSP | FRT |
| | MULTIPLE REGRESSION COEFFICIENT | $C_{Grip}$ | $C_{TUG}$ | $C_{Step}$ | $C_{X10m}$ | $C_{X5m}$ | $C_{PSP}$ | $C_{FRT}$ |
| GAIT DATA | PARAMETER | RIGHT-LEFT LOAD BALANCE | RIGHT-LEFT HEIGHT BALANCE | RATIO OF STEP WIDTH AND STEP LENGTH | LEFT HIP ROTATION | RIGHT HIP ROTATION | | |
| | SYMBOL | WBL | TBL | DY | L | R | | |
| | MULTIPLE REGRESSION COEFFICIENT | $C_{WBL}$ | $C_{TBL}$ | $C_{DY}$ | $C_L$ | $C_R$ | | |
| ACCELERATION DATA IN FIRST WALKING SECTION | PARAMETER | X-AXIS ACCELERATION INTEGRAL | Y-AXIS ACCELERATION INTEGRAL | Z-AXIS ACCELERATION INTEGRAL | ACCELERATION NORM INTEGRAL | | | |
| | SYMBOL | Axi | Ayi | Azi | Ai | | | |
| | MULTIPLE REGRESSION COEFFICIENT | $C_{Axi}$ | $C_{Ayi}$ | $C_{Azi}$ | $C_{Ai}$ | | | |
| ACCELERATION DATA IN SECOND WALKING SECTION | PARAMETER | X-AXIS ACCELERATION INTEGRAL | Y-AXIS ACCELERATION INTEGRAL | Z-AXIS ACCELERATION INTEGRAL | ACCELERATION NORM INTEGRAL | | | |
| | SYMBOL | Axc | Ayc | Azc | Ac | | | |
| | MULTIPLE REGRESSION COEFFICIENT | $C_{Axc}$ | $C_{Ayc}$ | $C_{Azc}$ | $C_{Ac}$ | | | |

FIG. 18

| RANK | RANGE | COMMENT |
|---|---|---|
| A | EstM > 28 | VERY GOOD. TRY TO KEEP GOOD CONDITION. |
| B | 28 ≧ EstM > 25 | GOOD. TRY TO KEEP GOOD CONDITION. |
| C | 25 ≧ EstM > 22 | AVERAGE. TRY TO KEEP GOOD CONDITION. |
| D | 22 ≧ EstM > 20 | ATTENTION IS REQUIRED TO SOME EXTENT. REGULAR EXERCISE WHILE USING YOUR HEAD, SUCH AS WALKING WHILE COUNTING, IS RECOMMENDED. |
| E | 20 ≧ EstM | ATTENTION IS REQUIRED. BRAIN CHECK TEST, ETC. ARE RECOMMENDED. |

FIG. 19

| AVERAGE SCORE | RANK | COMMENT |
|---|---|---|
| 1.0 OR MORE AND LESS THAN 1.5 | E | WORK HARDER. TRY TO IMPROVE STRENGTH WHILE AVOIDING FALLING, ETC. |
| 1.5 OR MORE AND LESS THAN 2.5 | D | WORK HARD. TRY NOT TO LOSE STRENGTH. |
| 2.5 OR MORE AND LESS THAN 3.5 | C | GOOD. TRY TO MAINTAIN GOOD HEALTH. |
| 3.5 OR MORE AND LESS THAN 4.5 | B | VERY GOOD. AIM FOR RANK A. |
| 4.5 OR MORE AND 5.0 OR LESS | A | EXCELLENT. TRY TO MAINTAIN THIS CONDITION. |

COGNITIVE FUNCTION EVALUATION DEVICE, COGNITIVE FUNCTION EVALUATION SYSTEM, COGNITIVE FUNCTION EVALUATION METHOD, AND RECORDING MEDIUM

CROSS-REFERENCE OF RELATED APPLICATIONS

This application is the U.S. National Phase under 35 U.S.C. § 371 of International Patent Application No. PCT/JP2019/008632, filed on Mar. 5, 2019, which in turn claims the benefit of Japanese Application No. 2018-057304, filed on Mar. 23, 2018, the entire disclosures of which Applications are incorporated by reference herein.

TECHNICAL FIELD

The present invention relates to a cognitive function evaluation device, a cognitive function evaluation system, a cognitive function evaluation method, and a recording medium.

BACKGROUND ART

Evaluation methods of evaluating cognitive function based on parameters measured from human walking are known.

PTL 1 discloses a method of evaluating the likelihood of senile disorders such as knee pain and low back pain, cognitive function, etc. based on data measured from human walking. The method disclosed in PTL 1 uses step rate, step length, step width, and the like as data measured from human walking, to evaluate physical frailty and cognitive frailty.

CITATION LIST

Patent Literature

PTL 1: Japanese Unexamined Patent Application Publication No. 2013-255786

SUMMARY OF THE INVENTION

Technical Problem

For example, when evaluating the degree of cognitive function, more accurate evaluation of cognitive function is desired.

The present invention provides a cognitive function evaluation device, etc. that can evaluate cognitive function accurately.

Solutions to Problem

A cognitive function evaluation device according to an aspect of the present invention includes: an obtainment unit configured to obtain, as gait data, at least one of first data and second data, the first data indicating a sway amount of a body of a subject during walking in a first walking section from start of walking of the subject to a predetermined number of steps, and the second data indicating a sway amount of the body of the subject during walking in a second walking section in a double task state in which the subject is walking while doing a given assignment, the second walking section being after the first walking section; a calculation unit configured to calculate, from the gait data obtained by the obtainment unit, a feature value that is based on the gait data; an evaluation unit configured to evaluate a cognitive function of the subject, based on the feature value calculated by the calculation unit; and an output unit configured to output an evaluation result of evaluation by the evaluation unit.

A cognitive function evaluation system according to an aspect of the present invention includes: the cognitive function evaluation device described above; and a body motion detection device that obtains the gait data and transmits the gait data to the cognitive function evaluation device.

A cognitive function evaluation method according to an aspect of the present invention is a cognitive function evaluation method executed by a computer, including: obtaining, as gait data, at least one of first data and second data, the first data indicating a sway amount of a body of a subject during walking in a first walking section from start of walking of the subject to a predetermined number of steps, and the second data indicating a sway amount of the body of the subject during walking in a second walking section in a double task state in which the subject is walking while doing a given assignment, the second walking section being after the first walking section; calculating, from the gait data obtained in the obtaining, a feature value that is based on the gait data; evaluating a cognitive function of the subject, based on the feature value calculated in the calculating; and outputting an evaluation result in the evaluating.

The present invention may be implemented as a non-transitory computer-readable recording medium having recorded thereon a program for causing a computer to execute the steps included in the cognitive function evaluation method.

Advantageous Effect of Invention

The cognitive function evaluation device, etc. according to an aspect of the present invention can evaluate cognitive function accurately.

BRIEF DESCRIPTION OF DRAWINGS

FIG. 15 is a flowchart illustrating a procedure by which the cognitive function evaluation device according to Embodiment 4 evaluates the cognitive function of a subject.

FIG. 16D is a diagram illustrating a fourth example of an image displayed on the display device by the cognitive function evaluation device according to Embodiment 4.

FIG. 17 is a diagram illustrating an example of parameters used when the cognitive function evaluation device according to Embodiment 4 calculates a feature value of the cognitive function of the subject.

FIG. 18 is a diagram illustrating an example of a table used when the cognitive function evaluation device according to Embodiment 4 ranks the cognitive function of the subject from the calculated feature value of the cognitive function of the subject.

FIG. 19 is a diagram illustrating an example of a table used when the cognitive function evaluation device according to Embodiment 4 ranks the motor function of the subject from the calculated motor feature value of the motor function of the subject.

DESCRIPTION OF EXEMPLARY EMBODIMENTS

A cognitive function evaluation device, etc. according to each embodiment will be described below, with reference to drawings. The embodiments described below each show a general or specific example. The numerical values, shapes, materials, structural elements, the arrangement and connection of the structural elements, steps, the processing order of the steps etc. shown in the following embodiments are mere examples, and do not limit the scope of the present invention. Of the structural elements in the embodiments described below, the structural elements not recited in any one of the independent claims representing the broadest concepts are described as optional structural elements.

Each drawing is a schematic and does not necessarily provide precise depiction. The substantially same structural elements are given the same reference marks throughout the drawings, and repeated description may be omitted or simplified.

Embodiment 1

[Structure]

First, structures of a cognitive function evaluation device and a cognitive function evaluation system according to Embodiment 1 will be described below, with reference to FIGS. 1 to 3.

Figure 1:
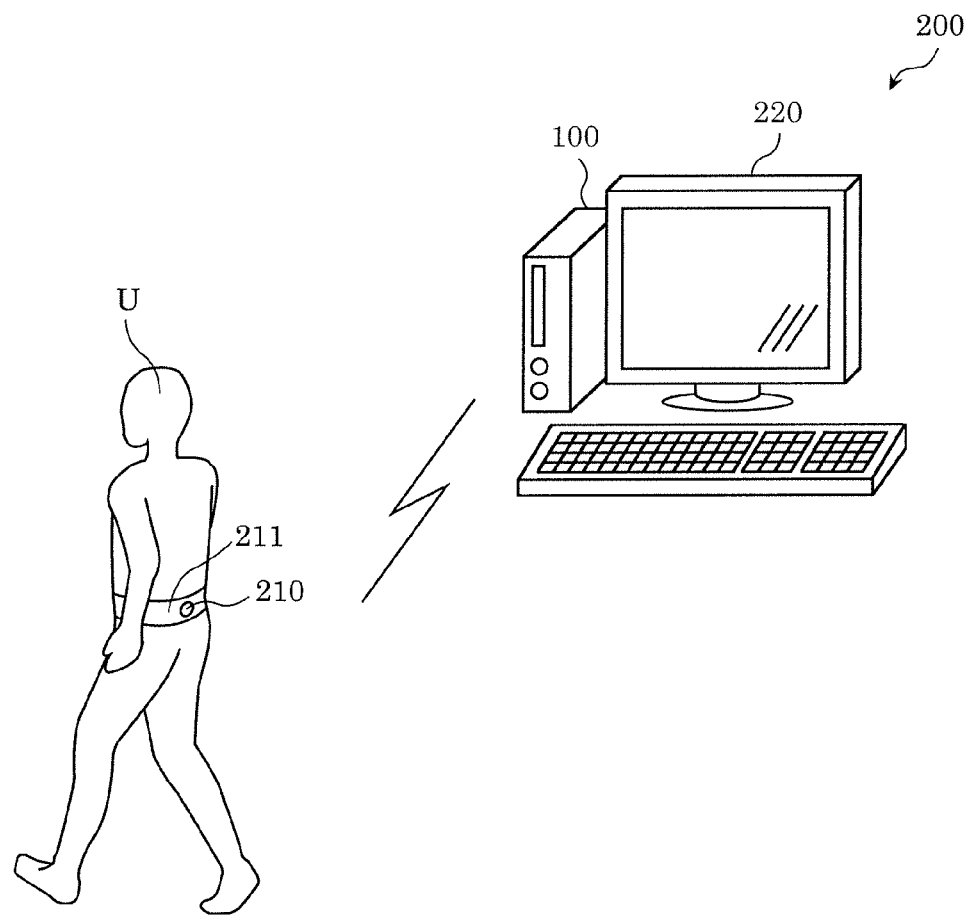
FIG. 1 is a diagram illustrating a structure of a system including a cognitive function evaluation device according to Embodiment 1.

FIG. 1 is a diagram illustrating a structure of a system including cognitive function evaluation device 100 according to Embodiment 1. FIG. 2 is a block diagram illustrating a characteristic functional structure of cognitive function evaluation device 100 according to Embodiment 1.

Cognitive function evaluation device 100 is a device for evaluating the degree of cognitive function of subject U by measuring the body sway of subject U. The cognitive function indicates the ability to recognize, remember, and judge. As a specific example, cognitive function evaluation device 100 evaluates whether a person has dementia (dementia patient). Dementia has symptoms of a decline in the foregoing cognitive function. A specific example of dementia is Alzheimer's dementia (Alzheimer's disease). Since dementia has no subjective symptoms, conventionally a family member of a dementia patient, a third party, or the like urges the dementia patient to go to hospital, so that the dementia patient seeks medical attention. As a result of a subject taking a batch test for diagnosis of dementia such as a cognitive function test, whether subject U has dementia can be determined.

However, the above-mentioned cognitive function test takes about 15 minutes. Besides, if the above-mentioned cognitive function test is conducted a plurality of times in a short period of time, the subject may memorize the answers.

It is known that a dementia patient differs in body sway during walking from a person without dementia (healthy subject).

Cognitive function evaluation device 100 is a device that evaluates the degree of cognitive function of subject U by measuring the body sway of subject U during walking.

Figure 2:
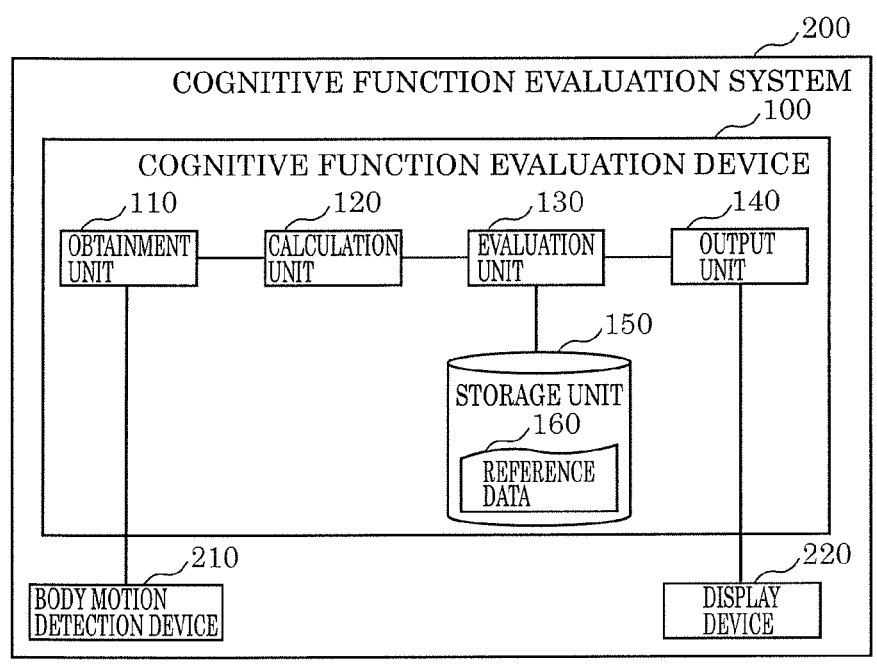
FIG. 2 is a block diagram illustrating a characteristic functional structure of the cognitive function evaluation device according to Embodiment 1.

Cognitive function evaluation system 200 includes, for example, cognitive function evaluation device 100, body motion detection device 210, and display device 220, as illustrated in FIGS. 1 and 2.

Body motion detection device 210 is a device that detects gait data indicating the sway amount of the body of subject U. In FIG. 1, an acceleration sensor is illustrated as an example of body motion detection device 210. Specifically, for example, subject U walks while wearing an acceleration sensor which is an example of body motion detection device 210 attached to wear tool 211 such as a belt. Acceleration data which is an example of the gait data of subject U during walking detected by the acceleration sensor is, for example, transmitted to cognitive function evaluation device 100 by a communication device (not illustrated).

Specifically, the acceleration sensor measures the acceleration of the part of subject U to which the acceleration sensor is attached, at a predetermined measurement rate. The measurement rate is the number of times the acceleration is measured per unit time. The acceleration sensor transmits the measured acceleration data to cognitive function evaluation device 100. Wear tool 211 includes a wireless communication device (not illustrated), and communicates with cognitive function evaluation device 100 through the wireless communication device. The acceleration sensor transmits the measured acceleration data to cognitive function evaluation device 100 by wireless communication. Wireless communication is performed in accordance with a predetermined wireless communication standard such as Bluetooth®, Wi-Fi®, or ZigBee®.

In the case where the acceleration sensor is a triaxial acceleration sensor, the acceleration data measured by the acceleration sensor is three-dimensional acceleration vector data, e.g. acceleration data in each of the front-back direction, the right-left direction (lateral direction), and the up-down direction of subject U. The acceleration data includes a plurality of measurement points. Each of the plurality of measurement points is associated with time information indicating the time at which the measurement point was measured.

In the case where body motion detection device 210 is an acceleration sensor, the acceleration sensor is not limited to a triaxial acceleration sensor, and may be a monoaxial acceleration sensor or a biaxial acceleration sensor.

Wear tool 211 is not limited to a belt, and may be clothing worn by subject U. For example, an acceleration sensor as an example of body motion detection device 210 may be fixed to the clothing, or contained in a pocket of the clothing.

Body motion detection device 210 is any device capable of detecting the sway amount of the body of subject U, and is not limited to an acceleration sensor and may be a camera for capturing an image of subject U walking, a radio wave sensor, or the like.

The gait data indicating the sway amount of the body of subject U detected by body motion detection device 210 may be transmitted to cognitive function evaluation device 100 by wireless communication, or transmitted to cognitive function evaluation device 100 by wire communication through a cable or the like.

Cognitive function evaluation device 100 is a device that obtains the sway amount indicating the degree of body sway of subject U detected by body motion detection device 210, evaluates the degree of cognitive function of subject U using the obtained sway amount, and outputs the evaluation result to display device 220. Cognitive function evaluation device 100 is, for example, a personal computer. Alternatively, cognitive function evaluation device 100 may be a server device.

Cognitive function evaluation device 100 includes obtainment unit 110, calculation unit 120, evaluation unit 130, output unit 140, and storage unit 150, as illustrated in FIG. 2.

Obtainment unit 110 obtains, as gait data, first data indicating the sway amount of the body of subject U during walking in a first walking section from the start of walking of subject U to a predetermined number of steps. The predetermined number of steps is any number of steps from when subject U starts walking to when the walking speed becomes approximately constant. The predetermined number of steps may be, but is not limited to, the number of steps from the start of walking to about the second, third, or fourth step.

Figure 3:
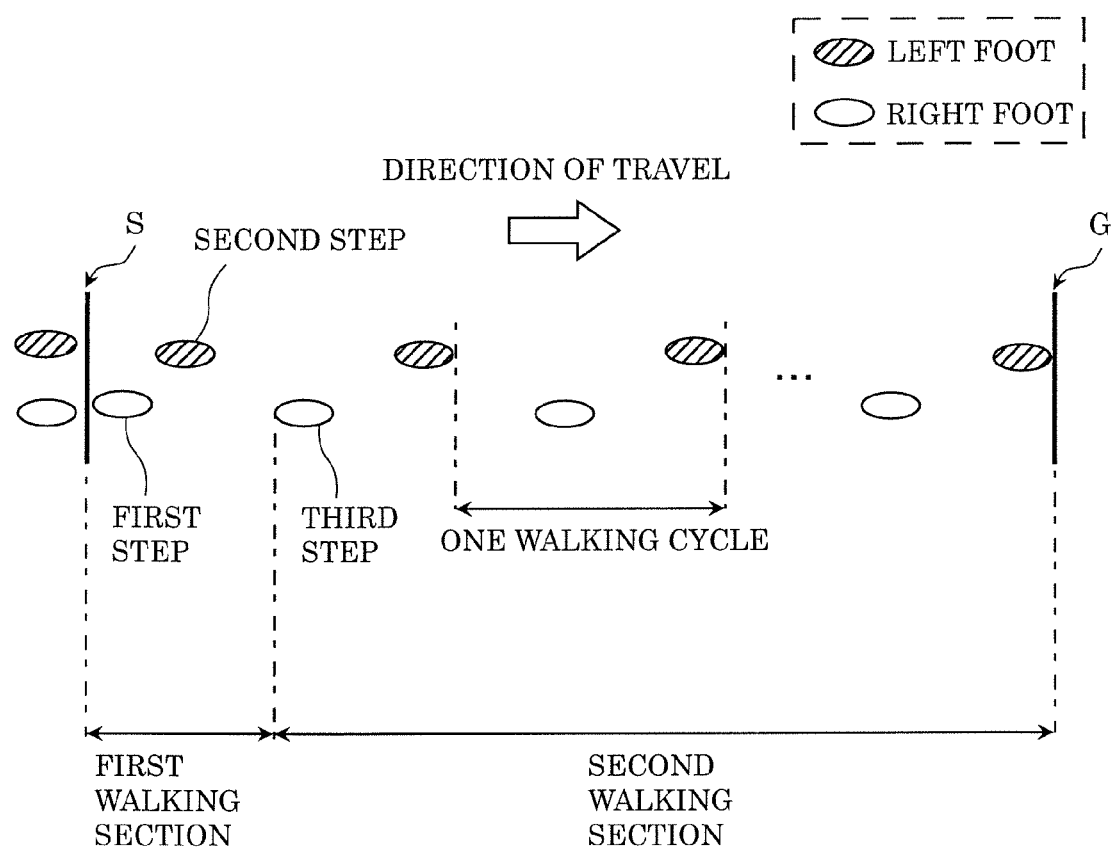
FIG. 3 is a conceptual diagram illustrating action of a person during walking.

FIG. 3 is a conceptual diagram illustrating action of a person during walking. In FIG. 3, the locations at which the person lands on the right foot and the left foot from walking start point S to walking end point G are indicated for illustrating the walking of the person. In FIG. 3, the locations at which the person lands on the right foot are indicated by white circles, and the locations at which the person lands on the left foot are indicated by hatched circles. In FIG. 3, the predetermined number of steps is the number of steps from when subject U starts walking at walking start point S to the second step.

As illustrated in FIG. 3, subject U stops once at walking start point S, and then walks to walking end point G. Obtainment unit 110 obtains, as the gait data, the first data indicating the sway amount of the body of subject U during walking in the first walking section from the start of walking of subject U at walking start point S to the predetermined number of steps.

Specifically, obtainment unit 110 obtains the first data indicating, as the sway amount of subject U during walking, the change amount of the displacement, speed, or acceleration.

For example, obtainment unit 110 obtains the first data indicating, as the sway amount of the body of subject U during walking, the change amount of the displacement, speed, or acceleration in the direction of travel of subject U.

Obtainment unit 110 may further obtain third data indicating the step length and step width of subject U in the first walking section.

The method of measuring the step length and the step width is not limited. As an example, in the case where body motion detection device 210 is an acceleration sensor, the step length and the step width may be calculated from the change amount of the acceleration of subject U during walking detected by body motion detection device 210. As another example, cognitive function evaluation system 200 may include a camera that captures an image of subject U during walking in order to measure the step length and the step width, and the step length and the step width may be measured by analyzing the image captured by the camera.

In such cases, the third data obtained by obtainment unit 110 may be the change amount of the acceleration or the image (or moving image), or values indicating the step length and the step width calculated from the change amount of the acceleration or the image (or moving image).

Obtainment unit 110 may further obtain fourth data indicating the walking speed of subject U in the first walking section. As an example, in the case where body motion detection device 210 is an acceleration sensor, the walking speed may be calculated from the change amount of the acceleration of subject U during walking detected by body motion detection device 210. As another example, cognitive function evaluation system 200 may include a camera that captures an image of subject U during walking and a clock unit such as a real time clock (RTC) that measures time, in order to measure the walking speed. The walking speed of subject U may be calculated from the position of subject U calculated by analyzing the image captured by the camera and the time measured by the clock unit.

In such cases, the fourth data obtained by obtainment unit 110 may be the change amount of the acceleration or the image (or moving image), or a value indicating the walking speed calculated from the change amount of the acceleration or the image (or moving image).

Obtainment unit 110 is, for example, a communication interface such as an adapter or a communication circuit for performing wire communication or wireless communication.

Calculation unit 120 calculates, from the gait data obtained by obtainment unit 110, a feature value based on the gait data. The feature value is a value calculated from the gait data by a predetermined method, and is a numeric value indicating the feature of walking of subject U. A specific calculation method for the feature value will be described later.

Moreover, calculation unit 120 calculates a frequency spectrum by performing frequency analysis on the change amount of the displacement, speed, or acceleration obtained by obtainment unit 110 as the first data. Calculation unit 120 calculates the feature value based on an integral at a higher specific frequency than the frequency corresponding to walking in the calculated frequency spectrum.

For example, calculation unit 120 may calculate, from the gait data including the first data and the third data obtained by obtainment unit 110, the feature value based on the gait data.

For example, calculation unit 120 may calculate, from the gait data including the first data, the third data, and the fourth data obtained by obtainment unit 110, the feature value based on the gait data.

Calculation unit 120 is, for example, implemented in terms of software by a control program stored in storage unit 150 and a central processing unit (CPU) that executes the control program. Calculation unit 120 may be implemented in terms of hardware by a dedicated circuit and the like, without using software.

Evaluation unit 130 evaluates the cognitive function of subject U, based on the feature value calculated by calculation unit 120.

Specifically, evaluation unit 130 checks the feature value calculated by calculation unit 120 against reference data 160 stored in storage unit 150, to evaluate the cognitive function of subject U. For example, storage unit 150 stores, as reference data 160, thresholds for the feature value for specifying the degree of cognitive function, with which healthy subjects, mild dementia patients, and dementia patients can be distinguished. Evaluation unit 130 compares the feature value calculated by calculation unit 120 with each threshold stored in reference data 160, to evaluate the degree of dementia.

Evaluation unit 130 is, for example, implemented in terms of software by a control program stored in storage unit 150 and a CPU that executes the control program. Evaluation unit 130 may be implemented in terms of hardware by a dedicated circuit and the like.

Calculation unit 120 and evaluation unit 130 may be implemented by one processor, microcomputer, or dedicated circuit having the functions of both units, or implemented by a combination of two or more processors, microcomputers, or dedicated circuits.

Output unit 140 outputs the evaluation result by evaluation unit 130.

Output unit 140 is, for example, a communication interface such as an adapter or a communication circuit for performing wire communication or wireless communication.

Storage unit 150 is memory storing reference data 160 indicating the relationship between the feature value of a person and the cognitive function of the person. Storage unit 150 is, for example, memory such as read only memory (ROM) and random access memory (RAM), and is formed by a hard disk drive (HDD), flash memory, or the like. Reference data 160 will be described in detail later.

Display device 220 is a device that displays the evaluation result of evaluation unit 130 transmitted from output unit 140. Display device 220 is, for example, implemented by a display and the like.

Output unit 140 outputs, for example, the evaluation result of evaluation unit 130 to display device 220 as image data. Display device 220 obtains the image data output from output unit 140, and displays an image based on the obtained image data.

The evaluation result of evaluation unit 130 may be output from output unit 140 as sound data. In this case, display device 220 may be, for example, a sound generation device such as an amplifier and a speaker, or a device including a display, an amplifier, a speaker, etc.

[Procedure]

A method of evaluating the cognitive function of subject U by cognitive function evaluation device 100 according to Embodiment 1 will be described in detail below, with reference to FIGS. 3 and 4.

Figure 4:
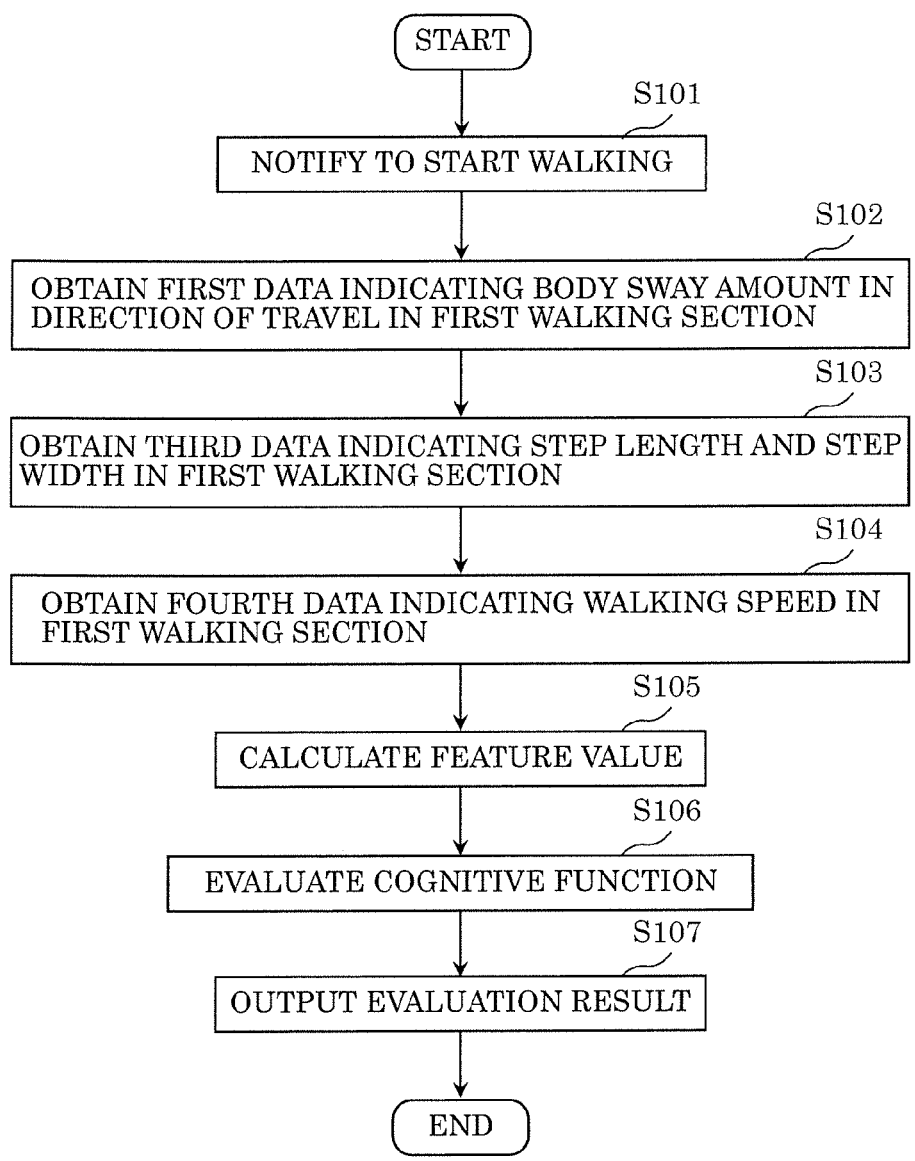
FIG. 4 is a flowchart illustrating a procedure by which the cognitive function evaluation device according to Embodiment 1 evaluates the cognitive function of a subject.

FIG. 4 is a flowchart illustrating a procedure by which cognitive function evaluation device 100 according to Embodiment 1 evaluates the cognitive function of subject U.

First, subject U moves to walking start point S illustrated in FIG. 3 and stops. Subsequently, subject U is notified to start walking (Step S101). Subject U starts walking. Cognitive function evaluation system 200 may, for example, include a position detection device such as a camera or a ranging sensor for detecting the position of subject U, and display, on display device 220, guidance or the like for instructing subject U to perform action depending on the position of subject U.

Next, obtainment unit 110 obtains the first data indicating the sway amount of the body in the direction of travel of subject U in the first walking section illustrated in FIG. 3, from body motion detection device 210 (Step S102).

Next, obtainment unit 110 obtains the third data indicating the step length and step width of subject U in the first walking section illustrated in FIG. 3 (Step S103).

Next, obtainment unit 110 obtains the fourth data indicating the walking speed of subject U in the first walking section illustrated in FIG. 3, from body motion detection device 210 (Step S104).

The first data, the third data, and the fourth data obtained by obtainment unit 110 in Steps S102 to S104 may be obtained in any order.

Next, calculation unit 120 calculates the feature value of subject U, based on the first data, the third data, and the fourth data obtained by obtainment unit 110 (Step S105).

Next, evaluation unit 130 evaluates the degree of cognitive function of subject U, based on the feature value of subject U calculated by calculation unit 120 (Step S106). Specifically, in Step S106, evaluation unit 130 evaluates the cognitive function of subject U by checking the feature value of subject U calculated by calculation unit 120 against reference data 160.

Lastly, output unit 140 outputs the evaluation result by evaluation unit 130 to display device 220 (Step S107).

Example

A result of calculating the feature value of subject U by cognitive function evaluation device 100 according to Embodiment 1 will be described in detail below, with reference to FIGS. 5A to 7.

Figure 5A:
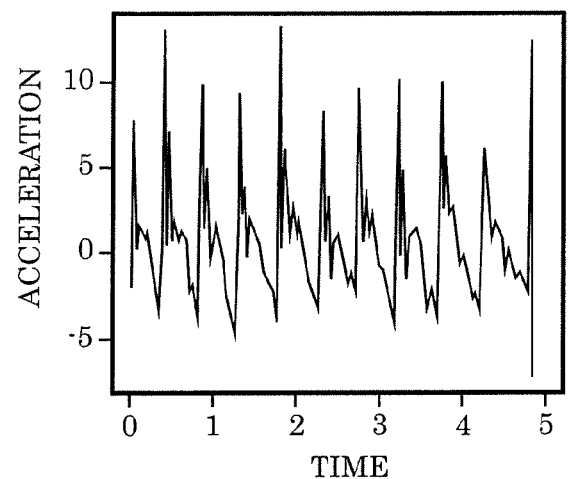
FIG. 5A is a diagram illustrating an example of data indicating acceleration with respect to time in the case where the subject is a healthy subject, which is obtained by the cognitive function evaluation device according to Embodiment 1.
Figure 5B:
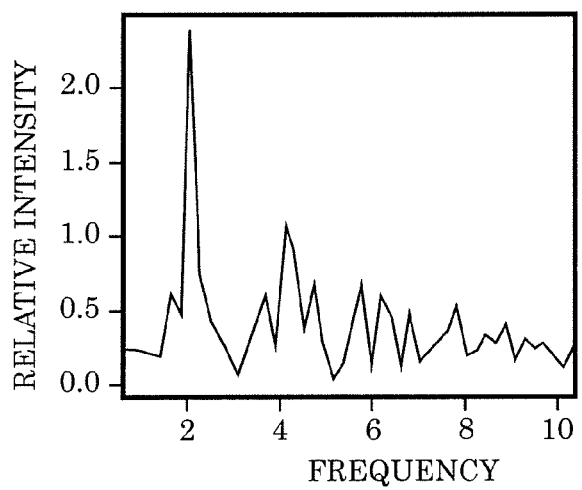
FIG. 5B is a diagram illustrating data obtained by Fourier transforming the data illustrated in FIG. 5A.
Figure 6A:
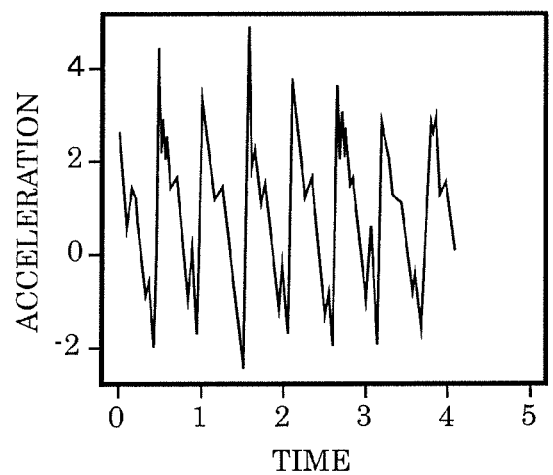
FIG. 6A is a diagram illustrating an example of data indicating acceleration with respect to time in the case where the cognitive function of the subject declines, which is obtained by the cognitive function evaluation device according to Embodiment 1.
Figure 6B:
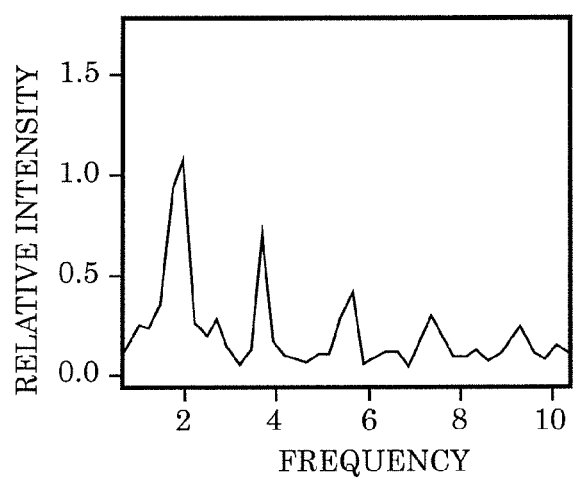
FIG. 6B is a diagram illustrating data obtained by Fourier transforming the data illustrated in FIG. 6A.

FIG. 5A is a diagram illustrating an example of data indicating acceleration with respect to time in the case where subject U is a healthy subject, which is obtained by cognitive function evaluation device 100 according to Embodiment 1. FIG. 5B is a diagram illustrating data obtained by Fourier transforming the data illustrated in FIG. 5A. FIG. 6A is a diagram illustrating an example of data indicating acceleration with respect to time in the case where the cognitive function of subject U declines, which is obtained by cognitive function evaluation device 100 according to Embodiment 1. FIG. 6B is a diagram illustrating data obtained by Fourier transforming the data illustrated in FIG. 6A.

The data illustrated in each of FIGS. 5A and 6A is data indicating the change amount of the acceleration in the direction of travel of subject U.

In the case where body motion detection device 210 is an acceleration sensor, for example, body motion detection device 210 detects the acceleration of subject U as illustrated in each of FIGS. 5A and 6A. That is, obtainment unit 110 obtains data indicating the change amount of the acceleration of subject U as illustrated in each of FIGS. 5A and 6A, for example, as the first data.

As illustrated in FIGS. 5B and 6B, in the frequency spectrum obtained by Fourier transforming the change amount of the acceleration with respect to time, the maximum peak is detected at about 2 Hz for both the healthy subject and the subject with declined cognitive function. This peak indicates the frequency corresponding to walking, and is equally detected for both the healthy subject and the subject with declined cognitive function.

On the other hand, an integral (area) at a specific frequency (e.g. 3 Hz or more) higher than the frequency corresponding to walking in the calculated frequency spectrum is different between the healthy subject and the subject with declined cognitive function. Hence, by adopting the integral at the specific frequency higher than the frequency corresponding to walking in the frequency spectrum as the feature value of subject U evaluated in cognitive function evaluation device 100, the degree of cognitive function can be evaluated accurately.

Figure 7:
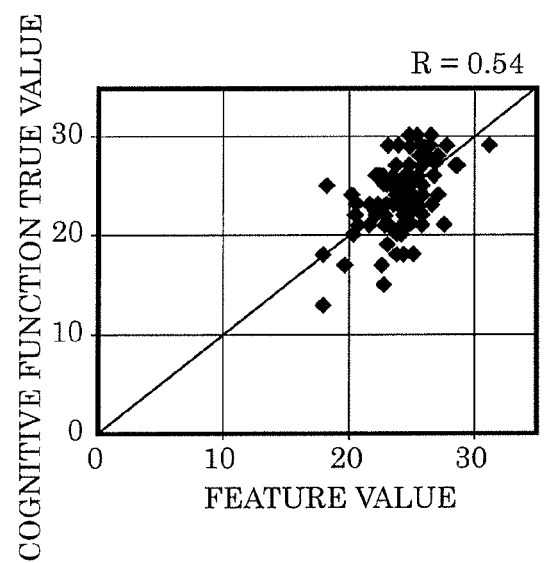
FIG. 7 is a diagram illustrating the correlation of the true value of the cognitive function of the subject to the value of evaluating the cognitive function of the subject by the cognitive function evaluation device according to Embodiment 1.

FIG. 7 is a diagram illustrating the correlation of the true value of the cognitive function of the subject to the value of evaluating the cognitive function of subject U by cognitive function evaluation device 100 according to Embodiment 1. Specifically, the horizontal axis in the graph illustrated in FIG. 7 represents the feature value of subject U calculated by cognitive function evaluation device 100. The vertical axis in the graph illustrated in FIG. 7 represents the value (cognitive function true value) which is a score when subject U whose feature value has been calculated by cognitive function evaluation device 100 underwent a batch test for determining the cognitive function. That is, when the values in the vertical axis and the horizontal axis in FIG. 7 are closer to each other, the accuracy with which cognitive function evaluation device 100 evaluates the degree of cognitive function of subject U is higher. In the graph illustrated in FIG. 7, the correlation coefficient was R=0.54.

The feature value illustrated in FIG. 7 was calculated according to the following Formula (1).

$$\text{(Feature value)} = a1 \times V + a2 \times \text{Age} + a3 \times Z16 + a4 \times DY + C \quad (1).$$

Herein, a1, a2, a3, and a4 are constants.

V is the walking speed of subject U in the first walking section.

Age is the age of subject U.

Z16 is the integral at 3 Hz or more in the frequency spectrum obtained from the change amount of the acceleration in the direction of travel of subject U in the first walking section.

DY is the ratio of the step length to the step width of subject U in the first walking section.

C is a constant.

As illustrated in FIG. 7, with cognitive function evaluation device 100, the feature value and the cognitive function true value are close to each other, so that the degree of cognitive function of subject U can be evaluated accurately.

The integral at the frequency adopted as Z16 may be the integral at 3 Hz or more, or the integral at 1 Hz to 3 Hz corresponding to a main frequency band by walking.

Effects, Etc

As described above, cognitive function evaluation device 100 according to Embodiment 1 includes: obtainment unit 110 configured to obtain, as gait data, first data indicating a sway amount of a body of subject U during walking in a first walking section from start of walking of subject U to a predetermined number of steps; calculation unit 120 configured to calculate, from the gait data obtained by obtainment unit 110, a feature value based on the gait data; evaluation unit 130 configured to evaluate a cognitive function of subject U, based on the feature value calculated by calculation unit 120; and output unit 140 configured to output an evaluation result of evaluation by evaluation unit 130.

With such a structure, cognitive function evaluation device 100 evaluates the cognitive function of subject U using the sway amount of the body of subject U during walking from the start of walking of subject U to the predetermined number of steps, which is an amount that tends to reflect the degree of cognitive function. Cognitive function evaluation device 100 can thus evaluate the cognitive function of subject U more accurately.

For example, obtainment unit 110 may obtain the first data indicating, as the sway amount of the body of subject U during walking, a change amount of a displacement, a speed, or an acceleration of subject U during walking.

Thus, cognitive function evaluation device 100 obtains the first data indicating, as the sway amount of the body of subject U during walking, the change amount of the displacement, speed, or acceleration of subject U during walking, which is easily detectable. This simplifies the structure.

For example, calculation unit 120 may calculate: a frequency spectrum by performing frequency analysis on the change amount of the displacement, speed, or acceleration of subject U during walking; and calculate the feature value, based on an integral at a specific frequency higher than a frequency corresponding to walking in the calculated frequency spectrum.

With such a structure, calculation unit 120 calculates the feature value based on a high frequency component that differs in the feature of the frequency spectrum depending on the degree of cognitive function. Thus, cognitive function evaluation device 100 can evaluate the degree of cognitive function of subject U more accurately.

For example, obtainment unit 110 may obtain the first data indicating, as the sway amount, the change amount of the displacement, speed, or acceleration of subject U during walking in a direction of travel of subject U.

In particular, the change amount of the acceleration in the direction of travel of subject U tends to differ depending on the degree of cognitive function in the first walking section.

Accordingly, by calculating the feature value based on the change amount of the acceleration in the direction of travel, cognitive function evaluation device 100 can evaluate the degree of cognitive function of subject U more accurately.

For example, obtainment unit 110 may further obtain third data indicating a step length and a step width of subject U in the first walking section, and calculation unit 120 may calculate, from the gait data including the first data and the third data obtained by obtainment unit 110, the feature value based on the gait data.

The step length and the step width in the first walking section also tend to differ depending on the degree of cognitive function. Accordingly, by calculating the feature value based on the step length and the step width, cognitive function evaluation device 100 can evaluate the degree of cognitive function of subject U more accurately.

Since the step length and the step width vary among individuals due to the leg length and the like, the ratio of the step length and the step width may be adopted as the third data.

For example, obtainment unit 110 may further obtain fourth data indicating a walking speed of subject U in the first walking section, and calculation unit 120 may calculate, from the gait data including the first data, the third data, and the fourth data obtained by obtainment unit 110, the feature value based on the gait data.

The walking speed in the first walking section also tends to differ depending on the degree of cognitive function. Accordingly, by calculating the feature value based on the walking speed, cognitive function evaluation device 100 can evaluate the degree of cognitive function of subject U more accurately.

For example, cognitive function evaluation device 100 may further include storage unit 150 configured to store reference data 160 indicating a relationship between a feature value of a person and a cognitive function of the person. Evaluation unit 130 may evaluate the cognitive function of subject U, by checking the feature value calculated by calculation unit 120 against reference data 160 stored in storage unit 150.

With such a structure, cognitive function evaluation device 100 can evaluate the degree of cognitive function of subject U by calculating the feature value from the obtained gait data and checking the calculated feature value against reference data 160. Accordingly, cognitive function evaluation device 100 can evaluate the cognitive function of subject U easily and accurately.

Embodiment 2

Cognitive function evaluation device 100 according to Embodiment 1 calculates the feature value based on the gait data of subject U in the first walking section illustrated in FIG. 3. A cognitive function evaluation device according to Embodiment 2 calculates the feature value based on the gait data of subject U in a second walking section illustrated in FIG. 3.

The cognitive function evaluation device, etc. according to Embodiment 2 will be described below. In the description of the cognitive function evaluation device, etc. according to Embodiment 2, structures that are substantially the same as the cognitive function evaluation device, etc. according to Embodiment 1 are given the same reference marks, and their description may be partly omitted or simplified.

[Structure]

Structures of the cognitive function evaluation device and cognitive function evaluation system according to Embodiment 2 will be described below, with reference to FIGS. 3 and 8.

Figure 8:
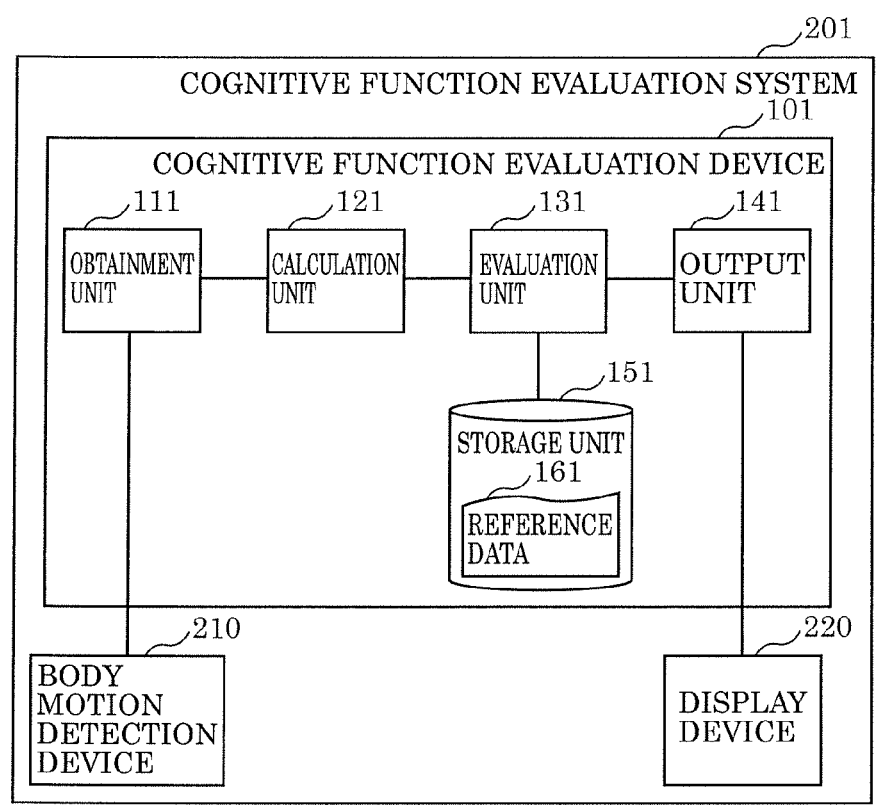
FIG. 8 is a block diagram illustrating a characteristic functional structure of a cognitive function evaluation device according to Embodiment 2.

FIG. 8 is a block diagram illustrating a characteristic functional structure of cognitive function evaluation system 201 and cognitive function evaluation device 101 according to Embodiment 2.

Cognitive function evaluation system 201 includes, for example, cognitive function evaluation device 101, body motion detection device 210, and display device 220, as illustrated in FIG. 8.

Cognitive function evaluation device 101 according to Embodiment 2 is a device for evaluating the degree of cognitive function of subject U by measuring the body sway of subject U, as with cognitive function evaluation device 100 according to Embodiment 1. Specifically, cognitive function evaluation device 101 is a device that obtains the sway amount indicating the degree of body sway of subject U detected by body motion detection device 210, evaluates the degree of cognitive function of subject U using the obtained sway amount, and outputs the evaluation result to display device 220. Cognitive function evaluation device 101 is, for example, a personal computer. Alternatively, cognitive function evaluation device 100 may be a server device.

Cognitive function evaluation device 101 includes obtainment unit 111, calculation unit 121, evaluation unit 131, output unit 141, and storage unit 151, as illustrated in FIG. 8.

Obtainment unit 111 obtains, as gait data, second data indicating the sway amount of the body of subject U during walking in the second walking section illustrated in FIG. 3 in a double task state in which subject U is walking while doing a given assignment. The assignment is not limited as long as it involves thinking. Examples include calculation and a quiz.

Specifically, obtainment unit 111 obtains the second data indicating, as the sway amount of subject U during walking, the change amount of the displacement, speed, or acceleration of subject U during walking.

For example, obtainment unit 111 obtains the second data indicating, as the sway amount of the body of subject U during walking, the change amount of the displacement, speed, or acceleration in a horizontal direction orthogonal to the direction of travel of subject U.

Obtainment unit 111 further obtains fifth data indicating the walking time of subject U in the second walking section. Cognitive function evaluation system 201 may include a camera that captures an image of subject U during walking and a clock unit such as a RTC that measures time, to measure the walking time. The walking time of subject U may be calculated from the position of subject U calculated by analyzing the image captured by the camera and the time measured by the clock unit. The fifth data obtained by obtainment unit 111 may be the image (or moving image) for measuring the walking time, or a value indicating the walking time calculated from the image (or moving image).

Obtainment unit 111 is, for example, a communication interface such as an adapter or a communication circuit for performing wire communication or wireless communication.

Calculation unit 121 calculates, from the gait data obtained by obtainment unit 111, a feature value based on the gait data. A specific calculation method for the feature value in Embodiment 2 will be described later.

Moreover, calculation unit 121 calculates a frequency spectrum by performing frequency analysis on the change amount of the displacement, speed, or acceleration obtained by obtainment unit 111 as the second data. Calculation unit 121 calculates the feature value based on an integral at a higher specific frequency than the frequency corresponding to walking in the calculated frequency spectrum.

For example, calculation unit 121 calculates, from the gait data including the second data and the fifth data obtained by obtainment unit 111, the feature value based on the gait data.

Calculation unit 121 is, for example, implemented in terms of software by a control program stored in storage unit 151 and a CPU that executes the control program. Calculation unit 121 may be implemented in terms of hardware by a dedicated circuit and the like.

Evaluation unit 131 evaluates the cognitive function of subject U, based on the feature value calculated by calculation unit 121.

Specifically, evaluation unit 131 checks the feature value calculated by calculation unit 121 against reference data 161 stored in storage unit 151, to evaluate the cognitive function of subject U.

Evaluation unit 131 is, for example, implemented in terms of software by a control program stored in storage unit 151 and a CPU that executes the control program. Evaluation unit 131 may be implemented in terms of hardware by a dedicated circuit and the like.

Calculation unit 121 and evaluation unit 131 may be implemented by one processor, microcomputer, or dedicated circuit having the functions of both units, or implemented by a combination of two or more processors, microcomputers, or dedicated circuits.

Output unit 140 outputs the evaluation result by evaluation unit 131.

Output unit 140 is, for example, a communication interface such as an adapter or a communication circuit for performing wire communication or wireless communication. For example, output unit 141 outputs the evaluation result of evaluation unit 131 to display device 220 as image data.

Storage unit 151 is memory storing reference data 161 indicating the relationship between the feature value of a person and the cognitive function of the person. Storage unit 151 is, for example, memory such as ROM and RAM, and is formed by a HDD, flash memory, or the like.

[Procedure]

A method of evaluating the cognitive function of subject U by cognitive function evaluation device 101 according to Embodiment 2 will be described in detail below, with reference to FIGS. 3 and 9.

Figure 9:
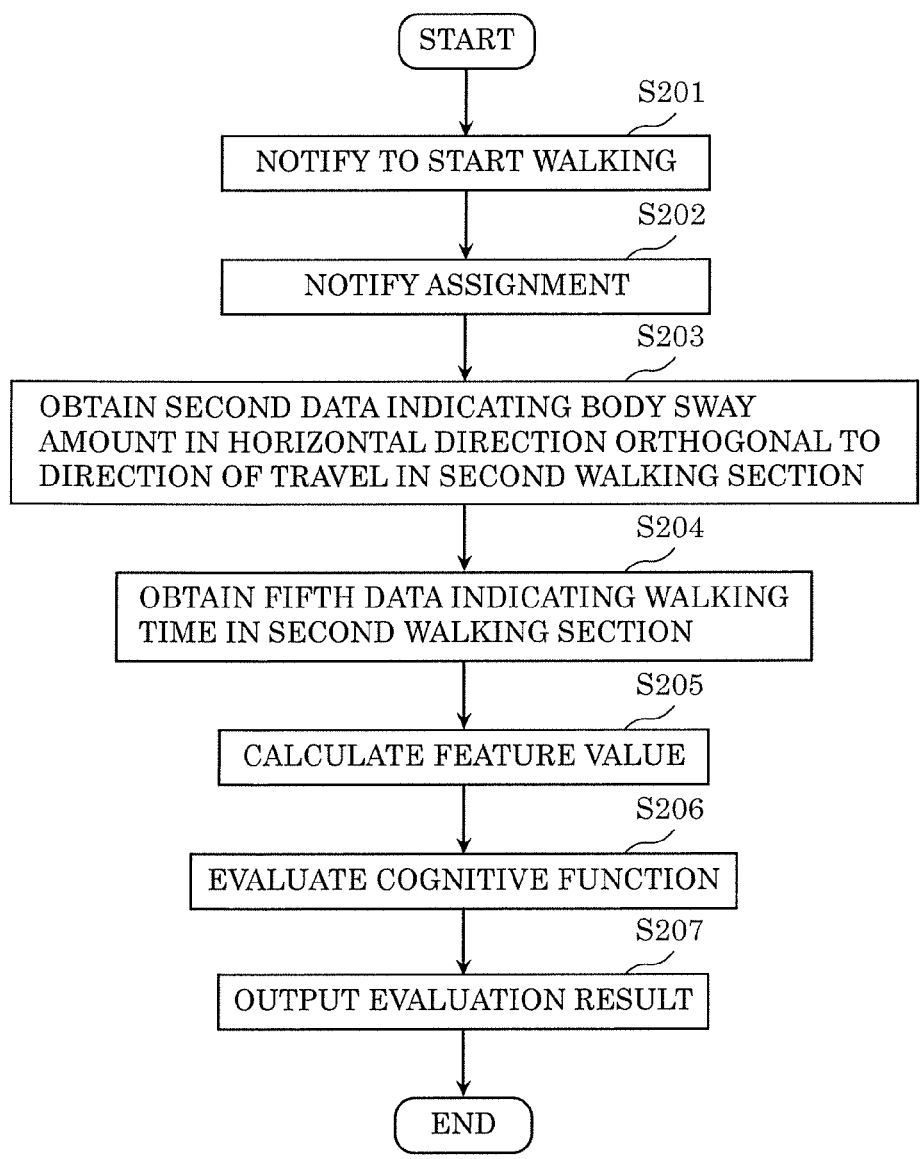
FIG. 9 is a flowchart illustrating a procedure by which the cognitive function evaluation device according to Embodiment 2 evaluates the cognitive function of a subject.

FIG. 9 is a flowchart illustrating a procedure by which cognitive function evaluation device 101 according to Embodiment 2 evaluates the cognitive function of subject U.

First, subject U moves to walking start point S illustrated in FIG. 3 and stops. Subsequently, subject U is notified to start walking (Step S201). Subject U starts walking. Cognitive function evaluation system 201 may, for example, include a position detection device such as a camera or a ranging sensor for detecting the position of subject U, and display, on display device 220, guidance or the like for instructing subject U to perform action depending on the position of subject U.

Next, before subject U enters the second walking section, subject U is notified of an assignment (Step S202). The timing at which subject U is notified of an assignment is not limited. Subject U may be notified before Step S201. In this case, in Step S202, immediately before (or immediately after) subject U enters the second walking section, subject U may be notified to do the assignment, instead of notifying subject U of the assignment. The notification of the assignment or the notification to do the assignment may be performed by cognitive function evaluation system 201 operating display device 220 or the like.

Thus, in cognitive function evaluation device 101 according to Embodiment 2, subject U is requested to walk in the second walking section while doing an assignment that involves thinking, and the sway amount of the body of subject U during walking is detected.

Next, obtainment unit 111 obtains the second data indicating the sway amount of the body in the horizontal direction orthogonal to the direction of travel of subject U (i.e. lateral direction of subject U) in the second walking section illustrated in FIG. 3, from body motion detection device 210 (Step S203).

Next, obtainment unit 111 obtains the fifth data indicating the walking time of subject U in the second walking section illustrated in FIG. 3 (Step S204).

The distance of the second walking section is not limited. For example, the distance of the second walking section may be at least about two or three walking cycles of subject U. In this embodiment, the distance from walking start point S to walking end point G is 8 m.

Next, calculation unit 121 calculates the feature value of subject U, based on the second data and the fifth data obtained by obtainment unit 111 (Step S205).

Next, evaluation unit 131 evaluates the degree of cognitive function of subject U, based on the feature value of subject U calculated by calculation unit 121 (Step S206). Specifically, in Step S206, evaluation unit 131 evaluates the cognitive function of subject U by checking the feature value of subject U calculated by calculation unit 121 against reference data 161.

Lastly, output unit 141 outputs the evaluation result by evaluation unit 131 to display device 220 (Step S207).

Example

A result of calculating the feature value of subject U by cognitive function evaluation device 101 according to Embodiment 2 will be described in detail below, with reference to FIG. 10.

Figure 10:
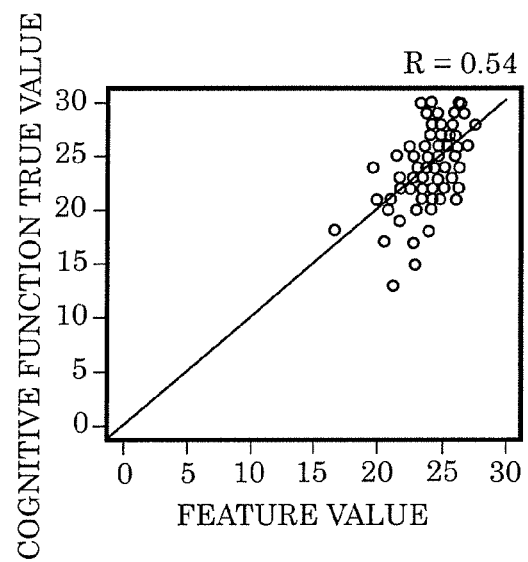
FIG. 10 is a diagram illustrating the correlation of the true value of the cognitive function of the subject to the value of evaluating the cognitive function of the subject by the cognitive function evaluation device according to Embodiment 2.

FIG. 10 is a diagram illustrating the correlation of the true value of the cognitive function of the subject to the value of evaluating the cognitive function of subject U by cognitive function evaluation device 101 according to Embodiment 2. Specifically, the horizontal axis in the graph illustrated in FIG. 10 represents the feature value of subject U calculated by cognitive function evaluation device 101. The vertical axis in the graph illustrated in FIG. 10 represents the value (cognitive function true value) which is a score when subject U whose feature value has been calculated by cognitive function evaluation device 101 underwent a batch test for determining the cognitive function. In the graph illustrated in FIG. 10, the correlation coefficient was R=0.54.

The feature value illustrated in FIG. 10 was calculated according to the following Formula (2).

$$\text{(Feature value)} = b0 + b1 \times T + b2 \times \text{Age} + b3 \times X36 \qquad (2).$$

Herein, b0, b1, b2, and b3 are constants.

T is the walking time of subject U in the second walking section.

Age is the age of subject U.

X36 is the integral at 3 Hz or more in the frequency spectrum obtained from the change amount of the acceleration in the horizontal direction orthogonal to the direction of travel of subject U in the second walking section.

As illustrated in FIG. 10, with cognitive function evaluation device 101, the feature value and the cognitive function true value are close to each other, so that the degree of cognitive function of subject U can be evaluated accurately.

The frequency used when calculating X36 may be 3 Hz or more. The frequency is not limited as long as it does not contain a main walking frequency found at about 2 Hz. For example, the frequency may be 4 Hz or more, and may be 6 Hz or more.

Effects, Etc

As described above, cognitive function evaluation device 101 according to Embodiment 2 includes: obtainment unit 111 configured to obtain, as gait data, second data indicating a sway amount of a body of subject U during walking in a second walking section in a double task state in which subject U is walking while doing a given assignment, the second walking section being after a first walking section from start of walking of subject U to a predetermined number of steps; calculation unit 121 configured to calculate, from the gait data obtained by obtainment unit 111, a feature value based on the gait data; evaluation unit 131 configured to evaluate a cognitive function of subject U, based on the feature value calculated by calculation unit 121; and output unit 141 configured to output an evaluation result of evaluation by evaluation unit 131.

With such a structure, cognitive function evaluation device 101 evaluates the cognitive function of subject U using the sway amount of the body of subject U during walking in the second walking section in a double task state in which the degree of cognitive function tends to show. Cognitive function evaluation device 101 can thus evaluate the cognitive function of subject U more accurately.

For example, obtainment unit 111 may obtain the second data indicating, as the sway amount of the body of subject U during walking, a change amount of a displacement, a speed, or an acceleration of subject U during walking.

For example, calculation unit 121 may calculate: a frequency spectrum by performing frequency analysis on the change amount of the displacement, speed, or acceleration of subject U during walking; and calculate the feature value, based on an integral at a specific frequency higher than a frequency corresponding to walking in the calculated frequency spectrum.

For example, obtainment unit 111 may obtain the second data indicating, as the sway amount, the change amount of the displacement, speed, or acceleration of subject U during walking in a horizontal direction orthogonal to a direction of travel of subject U.

In particular, the change amount of the acceleration in the horizontal direction orthogonal to the direction of travel of subject U (i.e. lateral direction of subject U) tends to differ depending on the degree of cognitive function in the second walking section. Accordingly, by calculating the feature value based on the change amount of the acceleration in the lateral direction of subject U, cognitive function evaluation device 101 can evaluate the degree of cognitive function of subject U more accurately.

For example, obtainment unit 111 may further obtain fifth data indicating a walking time of subject U in the second walking section, and calculation unit 121 may calculate, from the gait data including the second data and the fifth data obtained by obtainment unit 111, the feature value based on the gait data.

The walking time in the second walking section also tends to differ depending on the degree of cognitive function. Accordingly, by calculating the feature value based on the walking time, cognitive function evaluation device 101 can evaluate the degree of cognitive function of subject U more accurately.

Embodiment 3

Cognitive function evaluation device 100 according to Embodiment 1 calculates the feature value based on the gait data of subject U in the first walking section illustrated in FIG. 3. Cognitive function evaluation device 101 according to Embodiment 2 calculates the feature value based on the gait data of subject U in a second walking section illustrated in FIG. 3.

Further, a result of a functional reach test which is a method of evaluating the dynamic balance ability of subject U may be reflected in the evaluation of the degree of cognitive function.

The cognitive function evaluation device, etc. according to Embodiment 3 will be described below. In the description of the cognitive function evaluation device, etc. according to Embodiment 3, structures that are substantially the same as the cognitive function evaluation devices, etc. according to Embodiments 1 and 2 are given the same reference marks, and their description may be partly omitted or simplified.

[Structure]

Structures of the cognitive function evaluation device and cognitive function evaluation system according to Embodiment 3 will be described below, with reference to FIG. 11.

Figure 11:
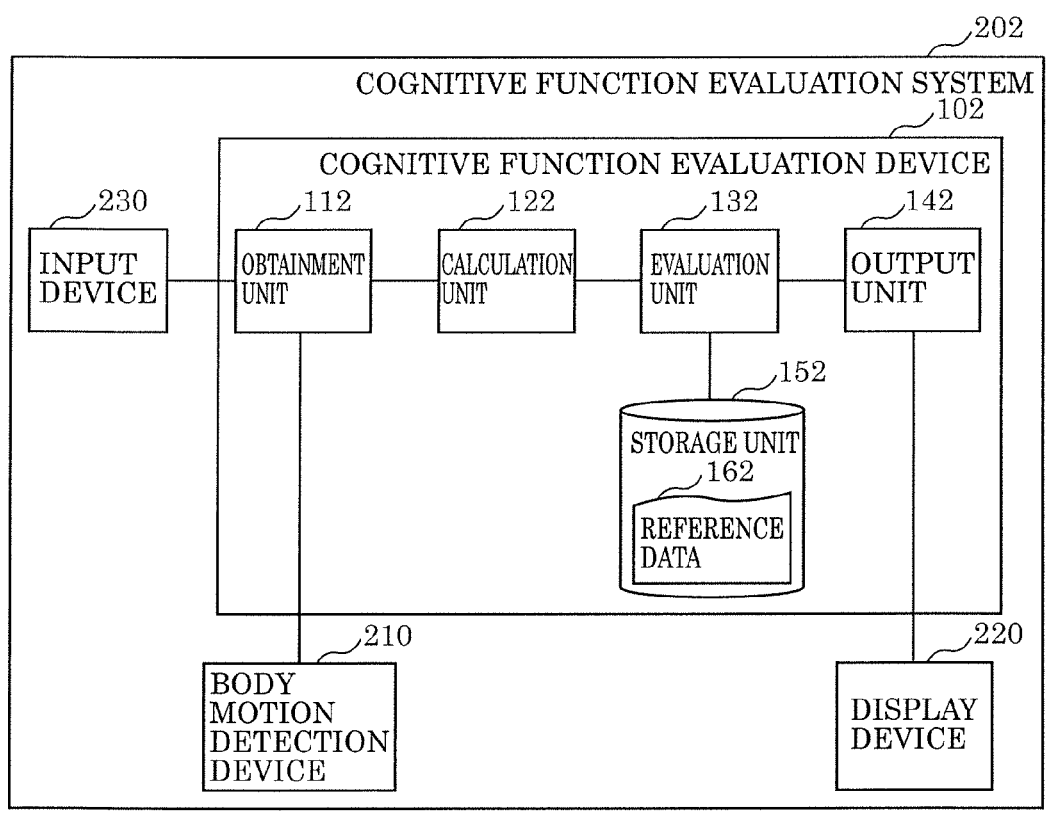
FIG. 11 is a block diagram illustrating a characteristic functional structure of a cognitive function evaluation device according to Embodiment 3.

FIG. 11 is a block diagram illustrating a characteristic functional structure of cognitive function evaluation system 202 and cognitive function evaluation device 102 according to Embodiment 3.

Cognitive function evaluation system 202 includes, for example, cognitive function evaluation device 102, body motion detection device 210, display device 220, and input device 230, as illustrated in FIG. 11.

Cognitive function evaluation device 102 according to Embodiment 3 is a device for evaluating the degree of cognitive function of subject U by measuring the body sway of subject U, as with cognitive function evaluation device 100 according to Embodiment 1. Specifically, cognitive function evaluation device 102 is a device that obtains the sway amount indicating the degree of body sway of subject U detected by body motion detection device 210, evaluates the degree of cognitive function of subject U using the obtained sway amount, and outputs the evaluation result to display device 220. Cognitive function evaluation device 102 is, for example, a personal computer. Alternatively, cognitive function evaluation device 100 may be a server device.

Input device 230 is an input mechanism for receiving an evaluation result of at least one of the dynamic balance ability and agility of subject U. For example, input device 230 is a user interface such as a button, a keyboard, a mouse, and a touch panel.

The dynamic balance ability denotes the balance ability when subject U is subjected to an external force while moving. For example, high dynamic balance ability means that subject U is unlikely to lose balance even when subjected to an external force while moving, e.g. walking.

The dynamic balance ability of subject U can be evaluated, for example, by the functional reach test.

The functional reach test is a test for evaluating the dynamic balance ability of subject U. Specifically, the functional reach test is a test of measuring the distance from the fingertip when the arm is raised 90 degrees in an upright posture to the fingertip when the arm is stretched forward as much as possible.

The agility of subject U can be evaluated, for example, based on the total physical reaction time, the number of steps, the number of taps, etc.

The total physical reaction time is the time from when subject U is stimulated to when subject U acts. For example, the total physical reaction time is the time from when subject U is stimulated by light, sound, or the like to when the foot of subject U leaves the ground.

The distance obtained by the functional reach test, the total physical reaction time, the number of steps per unit time, the number of taps per unit time, etc. for subject U are input to input device 230 as the evaluation result of the dynamic balance ability or agility.

Cognitive function evaluation device 102 according to Embodiment 3 evaluates the degree of cognitive function of subject U using the evaluation result of at least one of the dynamic balance ability and agility of subject U, in addition to the evaluation method of the cognitive function evaluation device according to Embodiment 1.

Cognitive function evaluation device 102 includes obtainment unit 112, calculation unit 122, evaluation unit 132, output unit 142, and storage unit 152, as illustrated in FIG. 11.

Obtainment unit 112 obtains, as gait data, the first data indicating the sway amount of the body of subject U during walking in the first walking section from the start of walking of subject U to the predetermined number of steps, as with obtainment unit 110. For example, obtainment unit 112 may further obtain the third data indicating the step length and step width of subject U in the first walking section. For example, obtainment unit 112 may further obtain the fourth data indicating the walking speed of subject U in the first walking section.

Obtainment unit 112 is, for example, a communication interface such as an adapter or a communication circuit for performing wire communication or wireless communication.

Obtainment unit 112 further obtains, as sixth data, the evaluation result of at least one of the dynamic balance ability and agility of subject U.

Calculation unit 122 calculates, from the gait data obtained by obtainment unit 112, a feature value based on the gait data.

For example, calculation unit 122 calculates, from the gait data including the first data and the sixth data obtained by obtainment unit 112, the feature value based on the gait data.

Calculation unit 122 is, for example, implemented in terms of software by a control program stored in storage unit 152 and a CPU that executes the control program. Calculation unit 122 may be implemented in terms of hardware by a dedicated circuit and the like.

Evaluation unit 132 evaluates the cognitive function of subject U, based on the feature value calculated by calculation unit 122.

Specifically, evaluation unit 132 checks the feature value calculated by calculation unit 122 against reference data 162 stored in storage unit 152, to evaluate the cognitive function of subject U.

Evaluation unit 132 is, for example, implemented in terms of software by a control program stored in storage unit 152 and a CPU that executes the control program. Evaluation unit 132 may be implemented in terms of hardware by a dedicated circuit and the like.

Calculation unit 122 and evaluation unit 132 may be implemented by one processor, microcomputer, or dedicated circuit having the functions of both units, or implemented by a combination of two or more processors, microcomputers, or dedicated circuits.

Output unit 142 outputs the evaluation result by evaluation unit 132. For example, output unit 142 outputs the evaluation result of evaluation unit 132 to display device 220 as image data.

Output unit 142 is, for example, a communication interface such as an adapter or a communication circuit for performing wire communication or wireless communication.

Storage unit 152 is memory storing reference data 162 indicating the relationship between the feature value of a person and the cognitive function of the person. Storage unit 152 is, for example, memory such as ROM and RAM, and is formed by a HDD, flash memory, or the like. Reference data 162 will be described in detail later.

[Procedure]

A method of evaluating the cognitive function of subject U by cognitive function evaluation device 102 according to Embodiment 3 will be described in detail below, with reference to FIGS. 3 and 12.

Figure 12:
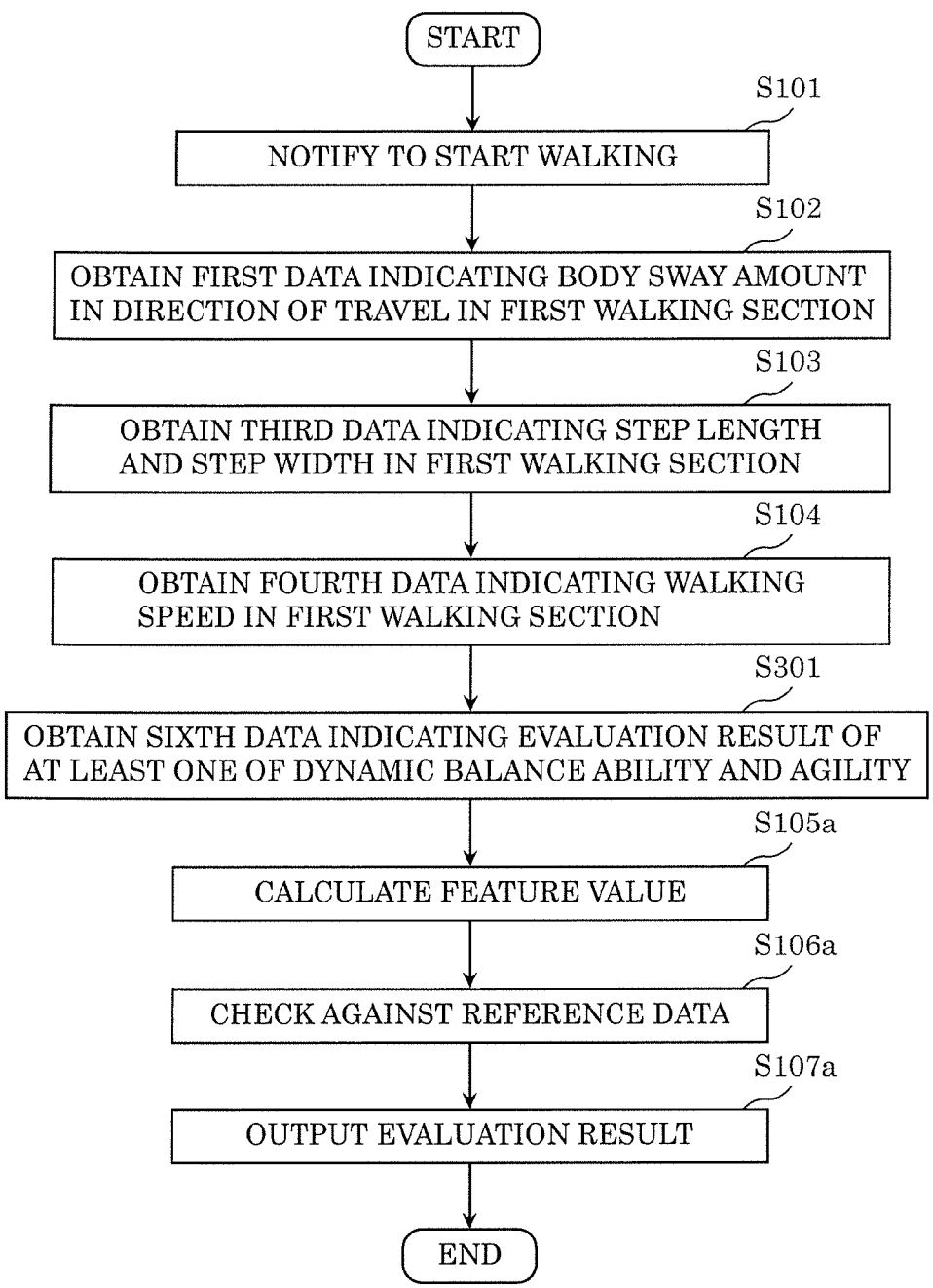
FIG. 12 is a flowchart illustrating a procedure by which the cognitive function evaluation device according to Embodiment 3 evaluates the cognitive function of a subject.

FIG. 12 is a flowchart illustrating a procedure by which cognitive function evaluation device 102 according to Embodiment 3 evaluates the cognitive function of subject U.

First, subject U moves to walking start point S illustrated in FIG. 3 and stops. Subsequently, subject U is notified to start walking (Step S101). Subject U starts walking.

Next, obtainment unit 112 obtains the first data indicating the sway amount of the body in the direction of travel of subject U in the first walking section illustrated in FIG. 3, from body motion detection device 210 (Step S102).

Next, obtainment unit 112 obtains the third data indicating the step length and step width of subject U in the first walking section illustrated in FIG. 3 (Step S103).

Next, obtainment unit 112 obtains the fourth data indicating the walking speed of subject U in the first walking section illustrated in FIG. 3, from body motion detection device 210 (Step S104).

Next, obtainment unit 112 obtains the sixth data indicating the evaluation result of at least one of the dynamic balance ability and agility of subject U (Step S301). In Step S301, for example, obtainment unit 112 obtains the distance obtained by the functional reach test for subject U as the evaluation result of the dynamic balance ability of subject U.

The first data, the third data, the fourth data, and the sixth data obtained by obtainment unit 110 in Steps S102 to S104 and S301 may be obtained in any order.

Next, calculation unit 122 calculates the feature value of subject U, based on the first data, the third data, the fourth data, and the sixth data obtained by obtainment unit 112 (Step S105a).

Next, evaluation unit 132 evaluates the degree of cognitive function of subject U, based on the feature value of subject U calculated by calculation unit 122 (Step S106a). Specifically, in Step S106a, evaluation unit 132 evaluates the cognitive function of subject U by checking the feature value of subject U calculated by calculation unit 122 against reference data 162.

Lastly, output unit 142 outputs the evaluation result by evaluation unit 132 to display device 220 (Step S107a).

Example

A result of calculating the feature value of subject U by cognitive function evaluation device 102 according to Embodiment 3 will be described in detail below, with reference to FIG. 13.

Figure 13:
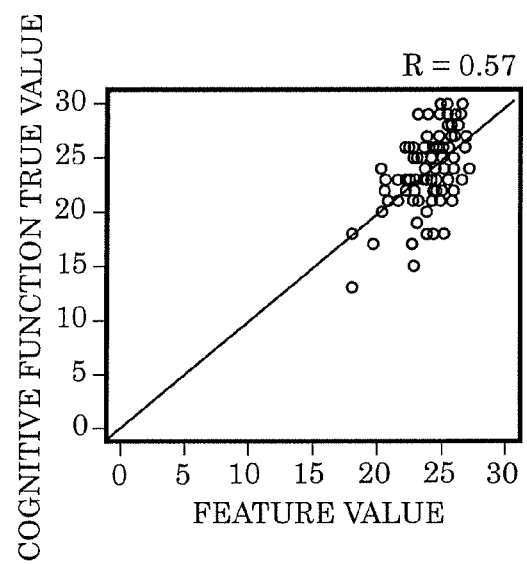
FIG. 13 is a diagram illustrating the correlation of the true value of the cognitive function of the subject to the value of evaluating the cognitive function of the subject by the cognitive function evaluation device according to Embodiment 3.

FIG. 13 is a diagram illustrating the correlation of the true value of the cognitive function of the subject to the value of evaluating the cognitive function of subject U by cognitive function evaluation device 102 according to Embodiment 3. Specifically, the horizontal axis in the graph illustrated in FIG. 13 represents the feature value of subject U calculated by cognitive function evaluation device 102. The vertical axis in the graph illustrated in FIG. 13 represents the value (cognitive function true value) which is a score when subject U whose feature value has been calculated by cognitive function evaluation device 102 underwent a batch test for determining the cognitive function. In the graph illustrated in FIG. 13, the correlation coefficient was R=0.57.

In this example, the result of the functional reach test was used as the evaluation result of at least one of the dynamic balance ability and agility, when calculating the feature value.

The feature value illustrated in FIG. 13 was calculated according to the following Formula (3).

$$\text{(Feature value)} = a0 + a1 \times V + a2 \times \text{Age} + a3 \times Z16 + a4 \times DY + a5 \times FRT \quad (3)$$

where a0 and a5 are constants.

FRT is the result of the functional reach test.

The other values are the same as in Formula (1).

As illustrated in FIG. 13, with cognitive function evaluation device 102, the feature value and the cognitive function true value are closer to each other than in the case of cognitive function evaluation device 100, so that the degree of cognitive function of subject U can be evaluated more accurately.

Effects, Etc

As described above, cognitive function evaluation device 102 according to Embodiment 3 has the same functional structure as cognitive function evaluation device 100 according to Embodiment 1, and obtainment unit 112 further obtains, as sixth data, an evaluation result of at least one of a dynamic balance ability and agility of subject U, and calculation unit 122 calculates, from the gait data including the first data and the sixth data obtained by obtainment unit 112, the feature value based on the gait data.

With such a structure, cognitive function evaluation device 102 can evaluate the cognitive function of subject U more accurately.

Embodiment 3 describes an example in which cognitive function evaluation device 100 according to Embodiment 1 evaluates the cognitive function of subject U by further using the evaluation result of at least one of the dynamic balance ability and agility. Alternatively, cognitive function evaluation device 101 according to Embodiment 2 may evaluate the cognitive function of subject U by further using the evaluation result of at least one of the dynamic balance ability and agility of subject U.

In detail, the obtainment unit in the cognitive function evaluation device according to the embodiment may further obtain, as sixth data, an evaluation result of at least one of a dynamic balance ability and agility of subject U, and the calculation unit may calculate, from the gait data including the sixth data and at least one of the first data and the second data obtained by the obtainment unit, the feature value based on the gait data.

Embodiment 4

The cognitive function evaluation devices according to Embodiments 1 to 3 each evaluate the degree of cognitive function of subject U and output the evaluation result.

A cognitive function evaluation device according to Embodiment 4 further evaluates the degree of motor function of subject U.

The cognitive function evaluation device, etc. according to Embodiment 4 will be described below. In the description of the cognitive function evaluation device, etc. according to Embodiment 4, structures that are substantially the same as the cognitive function evaluation devices, etc. according to Embodiments 1 to 3 are given the same reference marks, and their description may be partly omitted or simplified.

[Structure]

Structures of the cognitive function evaluation device and cognitive function evaluation system according to Embodiment 4 will be described below, with reference to FIG. 14.

Figure 14:
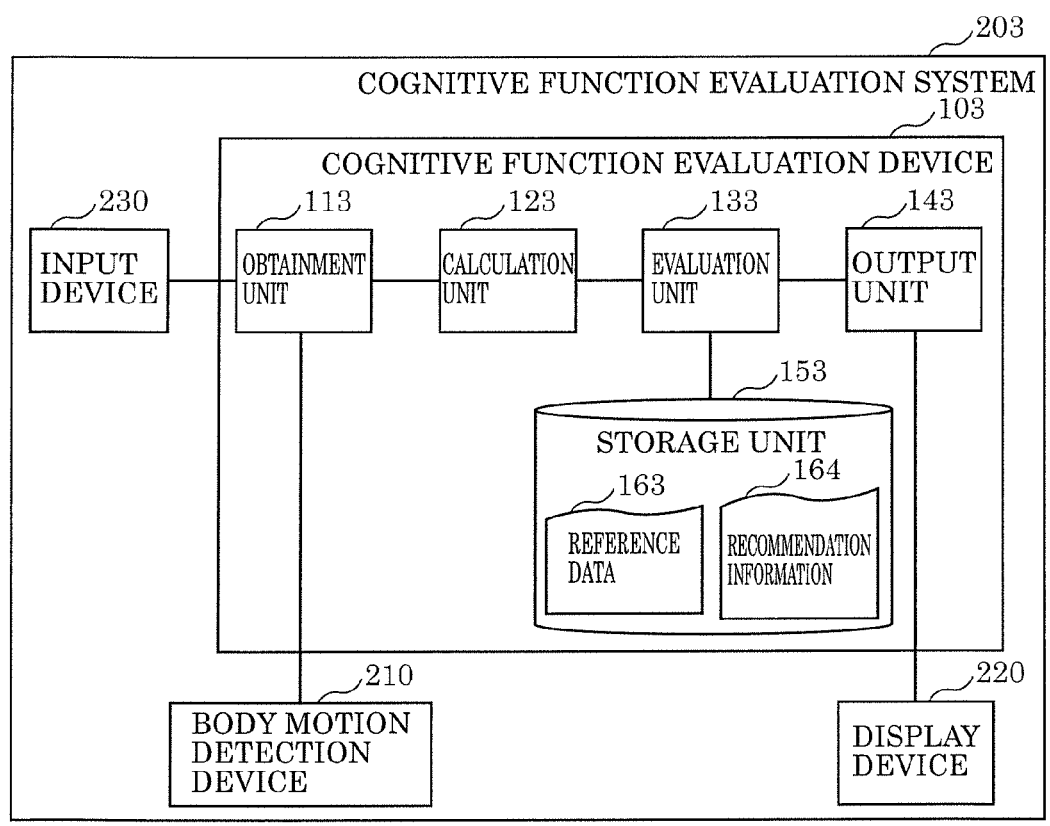
FIG. 14 is a block diagram illustrating a characteristic functional structure of a cognitive function evaluation device according to Embodiment 4.

FIG. 14 is a block diagram illustrating a characteristic functional structure of cognitive function evaluation system 203 and cognitive function evaluation device 103 according to Embodiment 4.

Cognitive function evaluation system 203 includes, for example, cognitive function evaluation device 103, body motion detection device 210, display device 220, and input device 230, as illustrated in FIG. 14.

Cognitive function evaluation device 103 according to Embodiment 4 is a device for evaluating the degree of cognitive function of subject U by measuring the body sway of subject U during walking, as with the cognitive function evaluation devices according to Embodiments 1 to 3. Specifically, cognitive function evaluation device 103 is a device that obtains the sway amount indicating the degree of body sway of subject U detected by body motion detection device 210, evaluates the degree of cognitive function of subject U using the obtained sway amount, and outputs the evaluation result to display device 220. Cognitive function evaluation device 103 is, for example, a personal computer. Alternatively, cognitive function evaluation device 100 may be a server device.

Input device 230 is an input mechanism for receiving an evaluation result of at least one of the dynamic balance ability and agility of subject U. For example, input device 230 is a user interface such as a button, a keyboard, a mouse, and a touch panel.

Cognitive function evaluation device 103 according to Embodiment 4 evaluates the degree of motor function of subject U using the evaluation result of at least one of the dynamic balance ability and agility of subject U, in addition to the evaluation of the cognitive function by the cognitive function evaluation devices according to Embodiments 1 to 3.

Cognitive function evaluation device 103 includes obtainment unit 113, calculation unit 123, evaluation unit 133, output unit 143, and storage unit 153, as illustrated in FIG. 14.

Obtainment unit 113 obtains, as gait data, the first data indicating the sway amount of the body of subject U during walking in the first walking section from the start of walking of subject U to the predetermined number of steps, as with obtainment unit 110. For example, obtainment unit 113 may further obtain the third data indicating the step length and step width of subject U in the first walking section. For example, obtainment unit 113 may further obtain the fourth data indicating the walking speed of subject U in the first walking section.

Obtainment unit 113 is, for example, a communication interface such as an adapter or a communication circuit for performing wire communication or wireless communication.

Obtainment unit 113 further obtains, as sixth data, the evaluation result of at least one of the dynamic balance ability and agility of subject U, as with obtainment unit 112.

Obtainment unit 113 may further obtain attribute information indicating an attribute of subject U. Herein, the attribute of subject U is, for example, age, gender, height, weight, etc., and the attribute information is information of such attribute. The attribute information of subject U may also include information about the health condition of subject U, such as information that subject U is wounded in the arm and the measurement of grip strength is difficult.

Calculation unit 123 calculates, from the gait data obtained by obtainment unit 113, a feature value based on the gait data.

For example, calculation unit 123 calculates, from the gait data including the first data and the sixth data obtained by obtainment unit 113 as described with regard to cognitive function evaluation device 102 according to Embodiment 3, the feature value (gait feature value) based on the gait data.

Calculation unit 123 is, for example, implemented in terms of software by a control program stored in storage unit 153 and a CPU that executes the control program. Calculation unit 123 may be implemented in terms of hardware by a dedicated circuit and the like.

Calculation unit 123 also calculates a motor feature value indicating the motor function of subject U, from the sixth data. The motor feature value is a value calculated from the sixth data by a predetermined method, and is a numeric value indicating the feature of walking of subject U. A specific calculation method for the motor feature value will be described later.

The sixth data used by calculation unit 123 in the calculation of the motor feature value may include data of measurement of muscle strength such as grip strength measurement data of subject U.

In the case where obtainment unit 113 obtains the attribute information of subject U, calculation unit 123 may calculate the motor feature value of subject U based on the attribute information and the sixth data.

For example, in the case where the attribute information includes information that subject U is wounded in the arm and the measurement of grip strength is difficult, calculation unit 123 does not take the grip strength measurement result into account when calculating the motor feature value.

Evaluation unit 133 evaluates the cognitive function of subject U, based on the feature value (gait feature value) calculated by calculation unit 123.

Specifically, evaluation unit 133 checks the feature value calculated by calculation unit 123 against reference data 163 stored in storage unit 153, to evaluate the cognitive function of subject U.

Evaluation unit 133 is, for example, implemented in terms of software by a control program stored in storage unit 153 and a CPU that executes the control program. Evaluation unit 133 may be implemented in terms of hardware by a dedicated circuit and the like.

Calculation unit 123 and evaluation unit 133 may be implemented by one processor, microcomputer, or dedicated circuit having the functions of both units, or implemented by a combination of two or more processors, microcomputers, or dedicated circuits.

Evaluation unit 133 further evaluates the motor function of subject U, based on the motor feature value calculated by calculation unit 123.

Moreover, evaluation unit 133 determines whether the cognitive function of subject U is evaluated higher than the motor function of subject U, based on predetermined evaluation criteria for the cognitive function and the motor function. For example, evaluation unit 133 ranks each of the cognitive function and the motor function on a scale of five: A, B, C, D, and E, based on evaluation criteria set beforehand. In the case where A is the best rank, i.e. the highest evaluation, and E is the worst rank, i.e. the lowest evaluation, evaluation unit 133 ranks the cognitive function and motor function of subject U based on the feature value (gait feature value) and the motor feature value calculated by calculation unit 123, to evaluate the cognitive function and motor function of subject U.

For example, in the case where evaluation unit 133 evaluates the cognitive function of subject U as rank A and evaluates the motor function of subject U as rank B, the cognitive function of subject U is evaluated higher than the motor function of subject U. In the following description, it is assumed that each of the cognitive function and the motor function is ranked on a scale of five: A, B, C, D, and E, where A is the best rank, i.e. the highest evaluation, and E is the worst rank, i.e. the lowest evaluation. The ranking may be not on a scale of five, but on a scale of four or less or on a scale of six or more. Moreover, in the case where each of the cognitive function and the motor function is ranked on a scale of five: A, B, C, D, and E, A may be the worst rank, i.e. the lowest evaluation, and E may be the best rank, i.e. the highest evaluation. The ranks are not limited to A, B, C, etc., and may be freely set, such as 1, 2, 3, etc.

Output unit 143 outputs the evaluation result by evaluation unit 133. For example, output unit 143 outputs the evaluation result of evaluation unit 132 to display device 220 as image data.

Output unit 143 is, for example, a communication interface such as an adapter or a communication circuit for performing wire communication or wireless communication.

Output unit 143 further outputs the evaluation result of the motor function of subject U by evaluation unit 133.

Moreover, in the case where evaluation unit 133 determines that the cognitive function of subject U is evaluated higher than the motor function of subject U, output unit 143 outputs first recommendation information which is information for subject U to improve the motor function. In the case where evaluation unit 133 determines that the cognitive function of subject U is evaluated not higher than the motor function of subject U, output unit 143 outputs second recommendation information which is information for subject U to improve the cognitive function. For example, the first recommendation information and the second recommendation information are stored in storage unit 153 as recommendation information 164. Evaluation unit 133 causes output unit 143 to selectively output the first recommendation information or the second recommendation information included in recommendation information 164, based on the evaluation results of the cognitive function and motor function of subject U.

Storage unit 153 is memory storing reference data 163 indicating the relationship between the feature value of a person and the cognitive function of the person. Storage unit 153 is, for example, memory such as ROM and RAM, and is formed by a HDD, flash memory, or the like. Reference data 163 is, for example, the same as reference data 162 stored in storage unit 152 in Embodiment 3.

Recommendation information 164 is information for subject U to improve the cognitive function or the motor function. For example, recommendation information 164 includes information, such as food information, exercise method, and exercise equipment use method, for promoting improvement in the motor function or the cognitive function. Output unit 143 outputs, as the first recommendation information, food information, exercise method, exercise equipment use method, etc. for promoting improvement particularly in the motor function in recommendation information 164, and outputs, as the second recommendation information, food information, exercise method, exercise equipment use method, etc. for promoting improvement particularly in the cognitive function in recommendation information 164.

[Procedure]

A method of evaluating the cognitive function of subject U by cognitive function evaluation device 103 according to Embodiment 4 will be described in detail below, with reference to FIG. 15.

First, obtainment unit 113 causes subject U to operate input device 230 to obtain information such as an identification (ID) of subject U (Step S401). In Step S401, obtainment unit 113 may cause subject U to operate input device 230 to obtain attribute information indicating the attribute of subject U.

Next, obtainment unit 113 obtains gait data and physical strength measurement data from subject U (Step S402). For example, in Step S402, obtainment unit 113 obtains the gait data of subject U (specifically, first data, third data, and fourth data) by performing Steps S101 to S104 in FIG. 4, and obtains the physical strength measurement data of subject U (specifically, sixth data) by performing Step S301 in FIG. 12.

Next, calculation unit 123 calculates the motor feature value indicating the motor function of subject U, based on the sixth data obtained by obtainment unit 113 (Step S403). In the case where obtainment unit 113 obtains the attribute information of subject U in Step S401, in Step S403 calculation unit 123 calculates the motor feature value indicating the motor function of subject U based on the attribute information and the sixth data obtained by obtainment unit 113.

Next, calculation unit 123 calculates the feature value indicating the degree of cognitive function of subject U, based on the gait data obtained by obtainment unit 113 (Step S404).

The order in which Steps S403 and S404 are performed is not limited, and Steps S403 and S404 may be performed in reverse order.

Next, evaluation unit 133 evaluates the degrees of cognitive function and motor function of subject U by ranking, based on the feature value and motor feature value of subject U calculated by calculation unit 123 (Step S405). Specifically, in Step S405, evaluation unit 133 evaluates the cognitive function and motor function of subject U by checking the feature value and motor feature value of subject U calculated by calculation unit 123 against reference data 163. That is, reference data 163 may include data indicating the relationship between the motor feature value of a person and the motor function of the person.

Next, output unit 143 outputs the evaluation results of the motor function and cognitive function of subject U by evaluation unit 133, to display device 220 (Step S406).

Next, evaluation unit 133 determines whether the cognitive function of subject U is evaluated higher than the motor function of subject U, based on the predetermined evaluation criteria for the cognitive function and the motor function (Step S407).

In the case where evaluation unit 133 determines that the cognitive function of subject U is evaluated higher than the motor function of subject U (Step S407: Yes), output unit 143 outputs the first recommendation information which is information for subject U to improve the motor function, as recommendation information 164 about the motor function (Step S408).

In the case where evaluation unit 133 determines that the cognitive function of subject U is evaluated not higher than the motor function of subject U (Step S407: No), output unit 143 outputs the second recommendation information which is information for subject U to improve the cognitive function, as recommendation information 164 about the cognitive function (Step S409).

Example

The steps performed by cognitive function evaluation device 103 according to Embodiment 4 in FIG. 15 will be described in detail below, with reference to FIGS. 16A to 19.

FIGS. 16A to 16D each illustrate an image which is a graphical user interface (GUI) displayed on a touch panel display in which input device 230 and display device 220 are integrated.

Figure 16A:
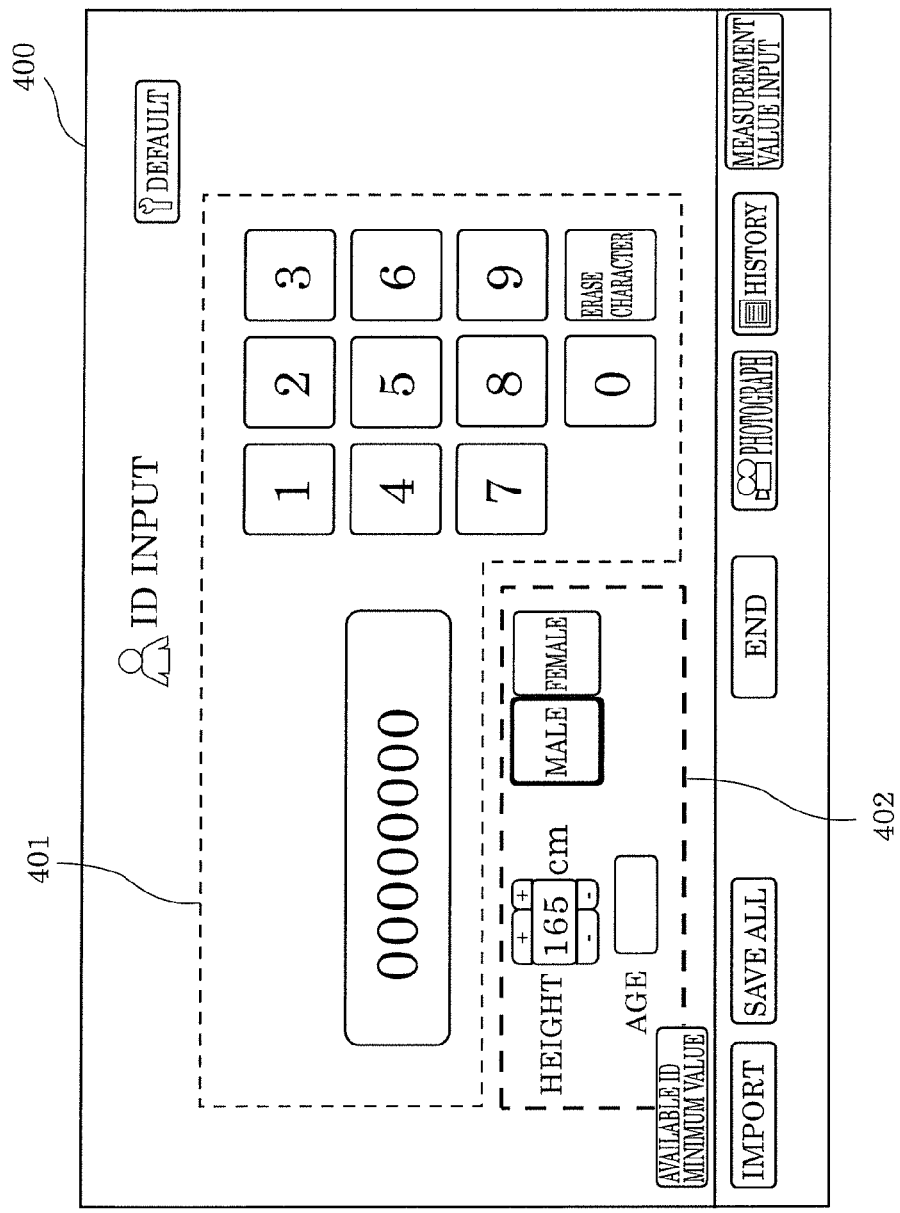
FIG. 16A is a diagram illustrating a first example of an image displayed on a display device by the cognitive function evaluation device according to Embodiment 4.

FIG. 16A is a diagram illustrating a first example of an image displayed on display device 220 by cognitive function evaluation device 103 according to Embodiment 4.

Image 400 illustrated in FIG. 16A is an image displayed on display device 220 to obtain the ID of subject U from subject U in Step S401 in FIG. 15.

Image 400 includes ID input portion 401 and attribute input portion 402.

ID input portion 401 is operated by subject U to receive input of the ID of subject U.

Attribute input portion 402 is operated by subject U to receive input of the attribute of subject U. In FIG. 16A, input of the height, gender, and age of subject U can be received as the attribute of subject U.

Figure 16B:
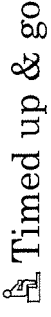
FIG. 16B is a diagram illustrating a second example of an image displayed on the display device by the cognitive function evaluation device according to Embodiment 4.

FIG. 16B is a diagram illustrating a second example of an image displayed on display device 220 by cognitive function evaluation device 103 according to Embodiment 4.

Image 410 illustrated in FIG. 16B is an image displayed on display device 220 to obtain the physical strength measurement data of subject U (i.e. sixth data) from subject U in Step S402 in FIG. 15.

Image 410 includes physical strength measurement data input portion 411.

Physical strength measurement data input portion 411 is operated by subject U to receive input of the physical strength measurement data of subject U. As illustrated in FIG. 16B, physical strength measurement data input portion 411 can receive input of results of various tests including a timed up & go test, a functional reach test, a test of single-leg standing with open eyes, a grip strength measurement test, a 5 m walking test, and a stepping test for subject U, as an example of the physical strength measurement data of subject U.

The timed up & go test is a test that measures the time from when subject U stands up from a state of sitting on a chair to when subject U sits on the chair again after turning around a mark 3 m ahead.

Figure 16C:
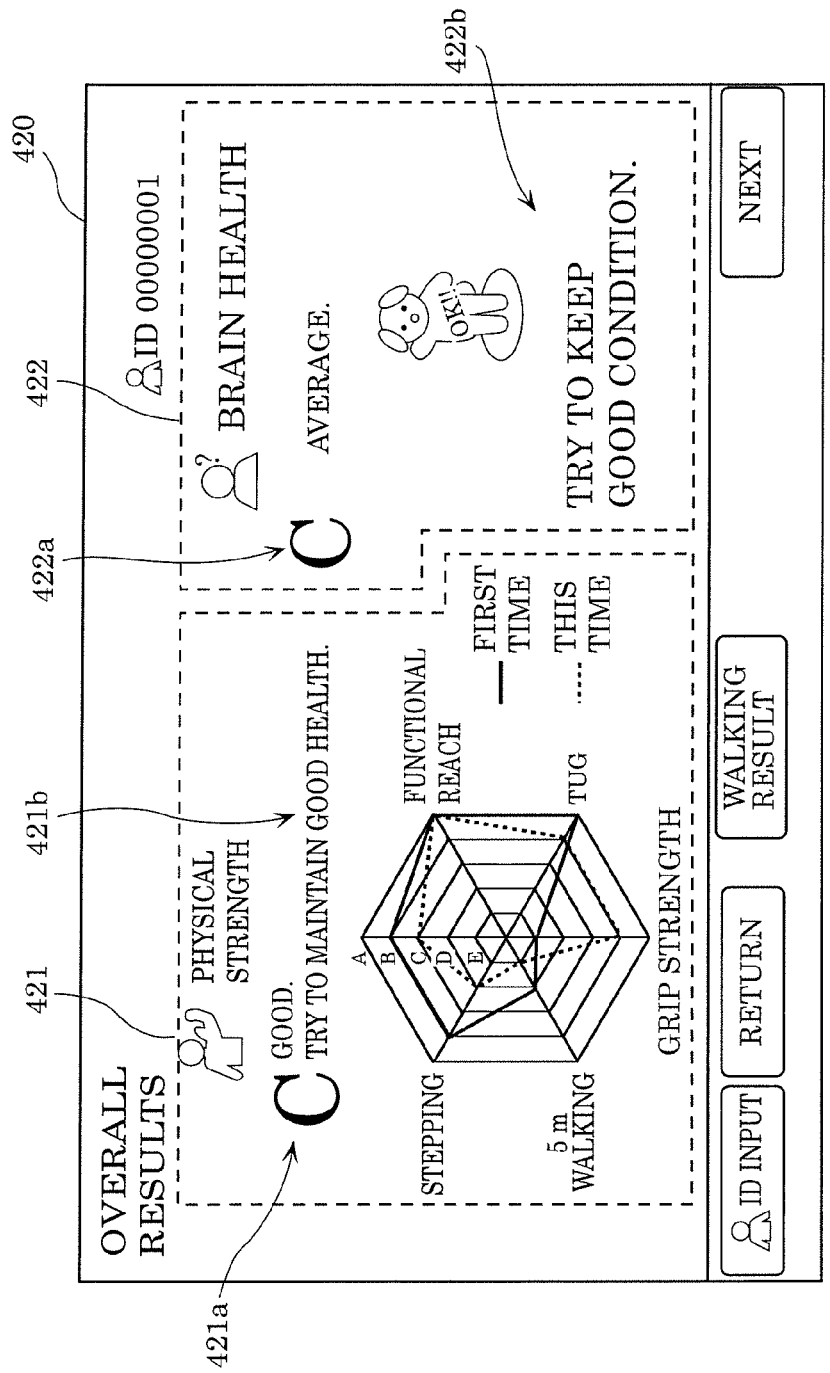
FIG. 16C is a diagram illustrating a third example of an image displayed on the display device by the cognitive function evaluation device according to Embodiment 4.

FIG. 16C is a diagram illustrating a third example of an image displayed on display device 220 by cognitive function evaluation device 103 according to Embodiment 4.

Image 420 illustrated in FIG. 16C is an image displayed on display device 220 to notify subject U of the evaluation results of the motor function and cognitive function of subject U in Step S406 in FIG. 15.

Image 420 includes motor function evaluation result notification portion 421 and cognitive function evaluation result notification portion 422.

Motor function evaluation result notification portion 421 is an image for notifying subject U of the evaluation of the motor function of subject U performed by evaluation unit 133 in Step S405 in FIG. 15. For example, motor function evaluation result notification portion 421 includes evaluation result 421a of the motor function of subject U by evaluation unit 133 in Step S405 in FIG. 15 and comment 421b based on evaluation result 421a.

Cognitive function evaluation result notification portion 422 is an image for notifying subject U of the evaluation of the cognitive function of subject U performed by evaluation unit 133 in Step S405 in FIG. 15. For example, cognitive function evaluation result notification portion 422 includes evaluation result 422a of the motor function of subject U by evaluation unit 133 in Step S405 in FIG. 15 and comment 422b based on evaluation result 422a.

Figure 16D:
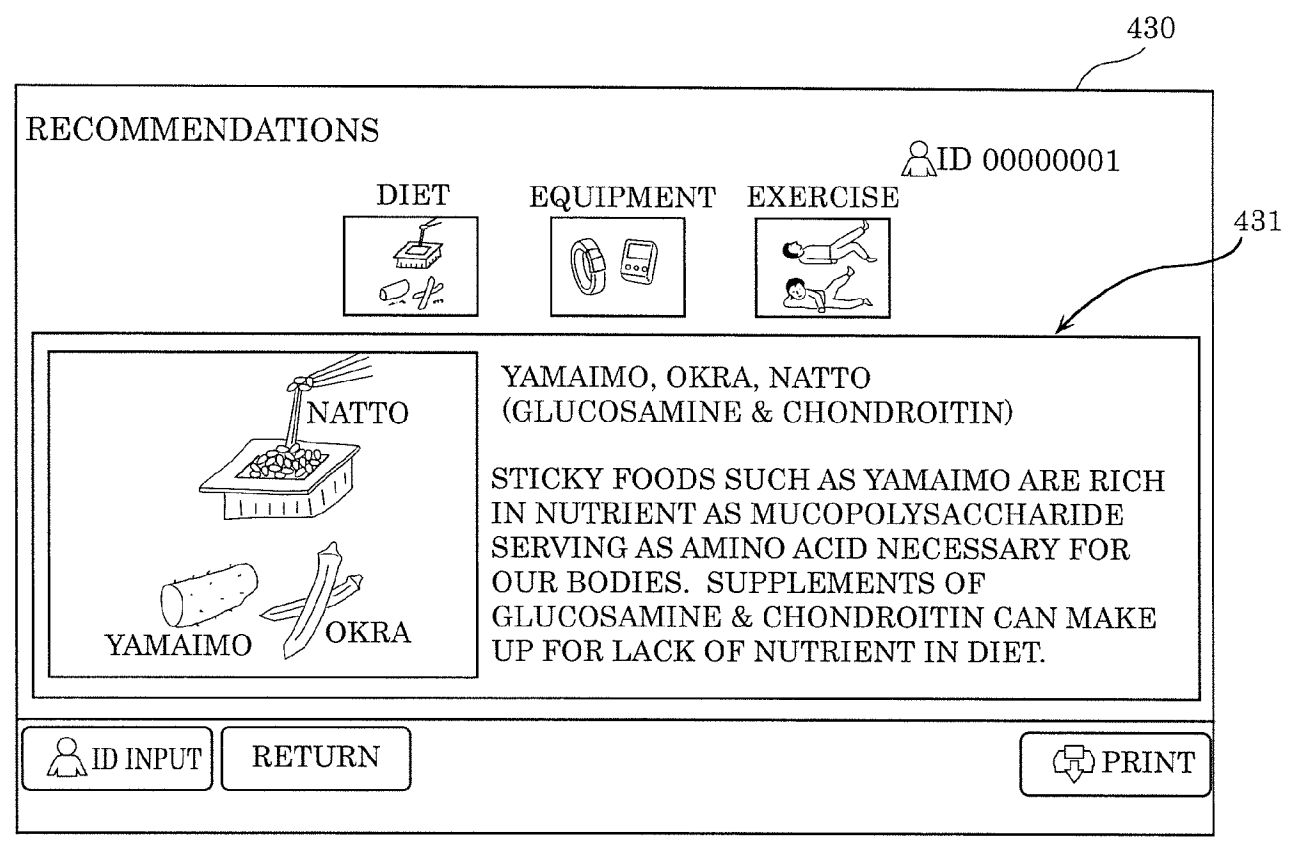

FIG. 16D is a diagram illustrating a fourth example of an image displayed on display device 220 by cognitive function evaluation device 103 according to Embodiment 4.

Image 430 illustrated in FIG. 16D is an image displayed on display device 220 to notify subject U of recommendation information 164 about the motor function or cognitive function of subject U in Step S408 or S409 in FIG. 15. As an example, image 430 shows the second recommendation information included in recommendation information 164 output in Step S409 in the case where evaluation unit 133 determines that the rank of the motor function and the rank of the cognitive function are both C as illustrated in FIG. 16C, that is, in the case where the determination in Step S407 in FIG. 15 results in No.

As illustrated in FIG. 16D, image 430 includes recommendation information display portion 431 for displaying recommendation information 164. Thus, by notifying, through recommendation information display portion 431, subject U of only recommendation information 164 about one of the motor function and the cognitive function that is determined as particularly bad by evaluation unit 133, information that is likely to be particularly useful for subject U can be notified, and also the amount of information notified can be reduced.

FIG. 17 is a diagram illustrating an example of parameters used when cognitive function evaluation device 103 according to Embodiment 4 calculates the feature value of the cognitive function of subject U. FIG. 18 is a diagram illustrating an example of a table used when cognitive function evaluation device 103 according to Embodiment 4 ranks the cognitive function of subject U from the calculated feature value of the cognitive function of subject U. In FIG. 18, EstM is the feature value calculated by calculation unit 123, and ranks A to E are ranks with which evaluation unit 133 performs evaluation from the feature value (EstM) calculated by calculation unit 123. Thus, for example, the table illustrated in FIG. 18 is stored in storage unit 153 as reference data 163.

Each multiple regression coefficient illustrated in FIG. 17 is any constant set beforehand. Each symbol illustrated in FIG. 17 is an actual measurement value of gait data or physical strength measurement data obtained from subject U or a numeric value of attribute. For example, in the case where the age of subject U is 25, symbol Age in FIG. 17 is 25. For example, in the case where the grip strength of subject U is 30 kgw, symbol Grip in FIG. 17 is 30. For parameters that are not numeric values such as gender, for example, numeric values determined according to any methods set beforehand, such as Gend=1 for male and Gend=2 for female, are adopted.

The feature value (EstM) illustrated in FIG. 18 is calculated, for example, according to the following Formula (4).

$$\text{EstM} = C_{Age} \times \text{Age} + C_{Gend} \times \text{Gend} + \ldots + C_{Ac} \times Ac + C_{EstM} \quad (4).$$

Here, $C_{EstM}$ is a constant.

In Formula (4), EstM is calculated by calculating, for each parameter in the table illustrated in FIG. 17, a result of multiplying the symbol and the multiple regression coefficient and calculating a sum of the resultant values, where description is omitted in part. For example, Formula (4) may further include $C_{Grip} \times \text{Grip}$ and the like as a numeric value to be added.

There is no need to adopt, in Formula (4), all parameters in the table illustrated in FIG. 17. For example, the parameter "grip strength" may not be adopted in Formula (4), based on the attribute of subject U. Thus, calculation unit 123 selects parameters to be used in Formula (4), based on the attribute information obtained by obtainment unit 113.

Evaluation unit 133 evaluates the cognitive function of subject U, by ranking the cognitive function of subject U from EstM calculated according to Formula (4). For example, in the case where EstM calculated by calculation unit 123 is 23, evaluation unit 133 ranks the cognitive function of subject U as "C". In this case, output unit 143 outputs information corresponding to comment 422b in cognitive function evaluation result notification portion 422 illustrated in FIG. 16C, such as "Average. Try to keep good condition." in the comment field illustrated in FIG. 18.

FIG. 19 is a diagram illustrating an example of a table used when cognitive function evaluation device 103 according to Embodiment 4 ranks the motor function of subject U from the calculated motor feature value of the motor function of subject U.

For example, calculation unit 123 performs evaluation on a scale of five: 5 points, 4 points, 3 points, 2 points, and 1 point, for each parameter based on a predetermined method. For example, for the parameter "grip strength", calculation unit 123 calculates a numeric value relating to the parameter "grip strength", such as 1 point when the grip strength is less than 10 kgw, 2 points when the grip strength is 10 kgw or more and less than 20 kgw, 3 points when the grip strength is 20 kgw or more and less than 30 kgw, 4 points when the grip strength is 30 kgw or more and less than 40 kgw, and 5 points when the grip strength is 40 kgw or more. Calculation unit 123 calculates a numeric value for each parameter, and calculates an average value of the numeric values as the motor feature value.

Evaluation unit 133 evaluates the motor function of subject U, by ranking the motor function of subject U from the calculated motor feature value. For example, in the case where the motor feature value calculated by calculation unit 123 is 3.0, evaluation unit 133 ranks the motor function of subject U as "C". Output unit 143 outputs information corresponding to comment 421b in motor function evaluation result notification portion 421 illustrated in FIG. 16C, such as "Good. Try to maintain good health." in the comment field illustrated in FIG. 19.

This evaluation method is an example, and the method of calculating the motor feature value is not limited. For example, evaluation may be performed on a scale of six or more or on a scale of four or less, for each parameter. The motor feature value may be an average value of the numeric values calculated from the respective parameters, and may be calculated in any way.

Although cognitive function evaluation device 103 evaluates the degree of cognitive function and the degree of motor function of subject U, for example, cognitive function evaluation device 103 may evaluate, as the degree of motor function, the degree of muscle strength function and the degree of balance function separately. Recommendation information 164 may then include recommendation information (third recommendation information) about the muscle strength function and recommendation information (fourth recommendation information) about the balance function.

In this case, evaluation unit 133 may rank each of the cognitive function, muscle strength function, and balance function of subject U, to evaluate the function. Output unit 143 may output, for example, recommendation information 164 about the function for which the evaluation result is lowest in rank. In the case where all of the functions are the same in rank, for example, output unit 143 may preferentially output recommendation information 164 about the cognitive function. In the case where the muscle strength function and the balance function are the same in rank, for example, output unit 143 may preferentially output recommendation information 164 about the muscle strength function.

Effects, Etc

As described above, cognitive function evaluation device 103 according to Embodiment 4 has the same functional structure as cognitive function evaluation device 102 according to Embodiment 3, and calculation unit 123 further calculates a motor feature value indicating a motor function of subject U from the sixth data, evaluation unit 133 further evaluates a motor function of subject U based on the motor feature value calculated by calculation unit 123, and output unit 143 further outputs an evaluation result of the motor function of subject U evaluated by evaluation unit 133.

With such a structure, cognitive function evaluation device 103 achieves the same effects as cognitive function evaluation device 102 according to Embodiment 3. Moreover, cognitive function evaluation device 103 can evaluate the motor function of subject U, in addition to the cognitive function of subject U. Cognitive function evaluation is not welcomed and is avoided by subject U in some cases. With cognitive function evaluation device 103, subject U does not know clearly whether the measurement results of walking-related measurement, a functional reach test, etc. are used in the evaluation of the cognitive function of subject U or in the evaluation of the motor function of subject U. Accordingly, with cognitive function evaluation device 103, the discomfort of subject U caused by being subjected to cognitive function evaluation can be reduced.

Some measurements such as walking-related measurement and a functional reach test are used in both cognitive function evaluation and motor function evaluation. Hence, cognitive function evaluation device 103 can use common data as part of the data used when calculating the feature value of the cognitive function and when calculating the motor feature value of the motor function. This can reduce the amount of data used in the calculation of the feature value of the cognitive function and the motor feature value of the motor function.

For example, evaluation unit 133 further determines whether the cognitive function of subject U is evaluated higher than the motor function of subject U based on predetermined evaluation criteria for the cognitive function and the motor function, and output unit 143: outputs first recommendation information for improving the motor function in the case where evaluation unit 133 determines that the cognitive function of subject U is evaluated higher than the motor function of subject U; and outputs second recommendation information for improving the cognitive function in the case where evaluation unit 133 determines that the cognitive function of subject U is evaluated not higher than the motor function of subject U.

With such a structure, cognitive function evaluation device 103 outputs only recommendation information 164 about one of the motor function and the cognitive function that is determined as particularly bad by evaluation unit 133, to subject U. Thus, cognitive function evaluation device 103 can notify information that is likely to be particularly useful for subject U, and also reduce the amount of information notified.

For example, in the case where the evaluation results of the cognitive function and motor function of subject U are the same, cognitive function evaluation device 103 preferentially outputs recommendation information 164 about the cognitive function. Thus, cognitive function evaluation device 103 can preferentially notify subject U of recommendation information 164 about the cognitive function that has a higher possibility of affecting the daily life of subject U in the future.

For example, obtainment unit 113 further obtains attribute information indicating an attribute of subject U, and calculation unit 123 calculates the motor feature value of subject U based on the attribute information and the sixth data obtained by obtainment unit 113.

With such a structure, cognitive function evaluation device 103 calculates the motor feature value in consideration of the age, gender, health condition, etc. of subject U. Thus, cognitive function evaluation device 103 calculates the motor feature value depending on subject U, with it being possible to output the evaluation result more suitable for subject U.

OTHER EMBODIMENTS

Although the cognitive function evaluation device, etc. according to each of Embodiments 1, 2, 3, and 4 have been described above, the present invention is not limited to the foregoing embodiments.

For example, in the foregoing embodiments, the processing units such as the calculation unit and the evaluation unit in the cognitive function evaluation device are implemented in terms of software by a processor executing a program. However, the present invention is not limited to such. The processing units may be implemented in terms of hardware by a dedicated electronic circuit using a gate array and the like.

In the foregoing embodiments, the cognitive function evaluation device evaluates the degree of cognitive function. However, for example, the cognitive function evaluation device may evaluate the degree of intoxication of the subject, instead of evaluating whether the subject has dementia.

In the foregoing embodiments, Alzheimer's dementia is used as a specific example of a symptom of cognitive function decrease. The cognitive function is the ability to recognize, remember, and judge, and dementia shows a symptom of a decrease in the cognitive function. Accordingly, the degree of the cognitive function evaluated by the cognitive function evaluation device is not limited to Alzheimer's dementia, and may be, for example, vascular dementia.

In the foregoing embodiments, to evaluate the cognitive function of the subject, data indicating the relationship between the score of the batch test such as a cognitive function test and the gait data indicating the body sway during walking is stored in the storage unit beforehand as the reference data. The reference data may be, however, any data with which the cognitive function can be evaluated by checking with the gait data indicating the body sway of the subject during walking. For example, the reference data may be data indicating the relationship between the score of Hasegawa's Dementia Scale-Revised (HDS-R) and the body sway during walking.

In the foregoing embodiments, the body motion detection device is an acceleration sensor as an example. However, the body motion detection device is not limited to such, as long as it is capable of detecting acceleration data indicating the body sway of the subject during walking. For example, the body motion detection device may be a camera or a radio wave sensor.

In the foregoing embodiments, the body motion detection device is communicably connected to the cognitive function evaluation device by wireless communication. However, the communication method is not limited to such. For example, the body motion detection device may include a wireless communication module or the like for wireless communication with the cognitive function evaluation device, and communicate with cognitive function evaluation device 100 via the wireless communication device. The body motion detection device transmits the measured acceleration data to cognitive function evaluation device 100 by wireless communication. Wireless communication may be performed, for example, in accordance with a predetermined wireless communication standard such as Bluetooth®, Wi-Fi®, or Zig-Bee®. The body motion detection device may perform wire communication with the cognitive function evaluation device. In this case, the body motion detection device may include a communication adapter and the like for connecting a cable for wire communication with the cognitive function evaluation device.

The present invention may be implemented as a method executed by the cognitive function evaluation device according to each of the foregoing embodiments. In detail, the present invention may be a cognitive function evaluation method executed by a computer, including: obtaining, as gait data, at least one of first data and second data, the first data indicating a sway amount of a body of a subject during walking in a first walking section from start of walking of the subject to a predetermined number of steps, and the second data indicating a sway amount of the body of the subject during walking in a second walking section in a double task state in which the subject is walking while doing a given assignment, the second walking section being after the first walking section; calculating, from the gait data obtained in the obtaining, a feature value that is based on the gait data; evaluating a cognitive function of the subject, based on the feature value calculated in the calculating; and outputting an evaluation result in the evaluating.

With such a method, the cognitive function of subject U can be accurately evaluated by the computer.

The present invention may be implemented as a program for causing a computer to execute the steps included in the foregoing cognitive function evaluation method. In other words, the present invention may be implemented as a program for causing a computer to execute the steps performed by the cognitive function evaluation device. The present invention may be implemented as a non-transitory computer-readable recording medium such as CD-ROM on which the program is recorded. The present invention may be implemented as information, data, or a signal indicating the program. The program, the information, the data, and the signal may be distributed via a communication network such as the Internet.

Thus, the cognitive function evaluation method can be executed by the computer as a program capable of accurately evaluating the cognitive function of subject U.

Other modifications obtained by applying various changes conceivable by a person skilled in the art to the embodiments and any combinations of the structural elements and functions in the embodiments without departing from the scope of the present invention are also included in the present invention.

The invention claimed is:

1. A cognitive function evaluation device, comprising:
an obtainment unit configured to obtain, as gait data, at least one of a first data and a second data,
the first data indicating a sway amount of a body of a subject during walking in a first walking section from start of walking of the subject to a predetermined number of steps starting at a time when the subject starts walking,
the second data indicating a sway amount of the body of the subject during walking in a second walking section in a double task state in which the subject is walking while doing a given assignment, the second walking section being after the first walking section,
the obtainment unit configured to determine that the second walking section starts when the predetermined number of steps have passed from the start of the first walking section, and
the obtainment unit further configured to obtain a physical strength measurement data of the subject using at least one of a dynamic balance ability and an agility of the subject;
a calculation unit configured to calculate, from the gait data obtained by the obtainment unit, a feature value that is based on the gait data and configured to calculate a motor feature value indicating a motor function of the subject using the physical strength measurement data;
an evaluation unit configured to evaluate a cognitive function and a motor function of subject based on the feature value and motor feature value of subject calculated by the calculation unit; and
an output unit configured to output evaluation results of the motor function and the cognitive function of the subject by the evaluation unit,
wherein the obtainment unit is configured to obtain the at least one of the first data and the second data each indicating, as the sway amount, a change amount of a displacement, a speed, or an acceleration of the subject during walking,
wherein the calculation unit is configured to:
calculate a frequency spectrum by performing frequency analysis on the change amount of the displacement of the subject during walking, the change amount of the speed of the subject during walking, or the change amount of the acceleration of the subject during walking; and
calculate the feature value, based on an integral at a specific frequency higher than a frequency corresponding to walking in the frequency spectrum calculated, the specific frequency being 3 Hz or more,
wherein degrees of cognitive function and motor function of the subject are determined, based on the feature value and motor feature value, and the output unit is further configured to control a display device to display an image that notifies the subject of the evaluation results of the motor function and cognitive function of the subject, wherein the image includes a motor function evaluation result notification portion and a cognitive function evaluation result notification portion, the motor function evaluation result notification portion notifies the subject of the evaluation of the motor function of the subject as performed by the evaluation unit, the motor function evaluation result notification portion including an evaluation result of the motor function of the subject by the evaluation unit and a comment based on the evaluation result being displayed on a same screen, the cognitive function evaluation result notification portion notifies the subject of the evaluation of the cognitive function of the subject performed by the evaluation unit, the cognitive function evaluation result notification portion including an evaluation result of the motor function of the subject by evaluation unit and a comment based on the evaluation result, and the motor function evaluation result notification portion and the cognitive function evaluation result notification portion being displayed simultaneously on a same screen.

2. The cognitive function evaluation device according to claim 1, wherein the obtainment unit is configured to obtain the first data indicating, as the sway amount, the change amount of the displacement of the subject during walking, the change amount of the speed of the subject during walking, or the change amount of the acceleration of the subject during walking in a direction of travel of the subject.

3. The cognitive function evaluation device according to claim 1, wherein the obtainment unit is further configured to obtain third data indicating a step length and a step width of the subject in the first walking section, and the calculation unit is configured to calculate, from the gait data including the first data and the third data obtained by the obtainment unit, the feature value that is based on the gait data.

4. The cognitive function evaluation device according to claim 3, wherein the obtainment unit is further configured to obtain fourth data indicating a walking speed of the subject in the first walking section, and the calculation unit is configured to calculate, from the gait data including the first data, the third data, and the fourth data obtained by the obtainment unit, the feature value that is based on the gait data.

5. The cognitive function evaluation device according to claim 1, wherein the obtainment unit is configured to obtain the second data indicating, as the sway amount, the change amount of the displacement of the subject during walking, the change amount of the speed of the subject during walking, or the change amount of the acceleration of the subject during walking in a horizontal direction orthogonal to a direction of travel of the subject.

6. The cognitive function evaluation device according to claim 5, wherein the obtainment unit is further configured to obtain fifth data indicating a walking time of the subject in the second walking section, and the calculation unit is configured to calculate, from the gait data including the second data and the fifth data obtained by the obtainment unit, the feature value that is based on the gait data.

7. The cognitive function evaluation device according to claim 1, wherein the obtainment unit is further configured to obtain, as sixth data, an evaluation result of at least one of a dynamic balance ability and agility of the subject, and the calculation unit is configured to calculate, from the gait data including the sixth data and the at least one of the first data and the second data obtained by the obtainment unit, the feature value that is based on the gait data.

8. The cognitive function evaluation device according to claim 7, wherein the calculation unit is further configured to calculate a motor feature value indicating the motor function of the subject, from the sixth data, the evaluation unit is further configured to evaluate the motor function of the subject, based on the motor feature value calculated by the calculation unit.

9. The cognitive function evaluation device according to claim 8, wherein the evaluation unit is further configured to determine whether the cognitive function of the subject is evaluated higher than the motor function of the subject, based on predetermined evaluation criteria for the cognitive function and the motor function, and the output unit is configured to:

output first recommendation information for improving the motor function, when the evaluation unit determines that the cognitive function of the subject is evaluated higher than the motor function of the subject; and output second recommendation information for improving the cognitive function, when the evaluation unit determines that the cognitive function of the subject is evaluated not higher than the motor function of the subject.

10. The cognitive function evaluation device according to claim 8, wherein the obtainment unit is further configured to obtain attribute information indicating an attribute of the subject, and the calculation unit is configured to calculate the motor feature value of the subject, based on the attribute information and the sixth data obtained by the obtainment unit.

11. The cognitive function evaluation device according to claim 1, further comprising:

a storage unit configured to store reference data indicating a relationship between a feature value of a person and a cognitive function of the person, and the evaluation unit is configured to evaluate the cognitive function of the subject, by checking the feature value calculated by the calculation unit against the reference data stored in the storage unit.

12. A cognitive function evaluation system comprising:
the cognitive function evaluation device according to claim 1; and
a body motion detection device that obtains the gait data and transmits the gait data to the cognitive function evaluation device.

13. A cognitive function evaluation method executed by a computer, the cognitive function evaluation method comprising:
obtaining, as gait data, at least one of first data and second data, the first data indicating a sway amount of a body of a subject during walking in a first walking section from start of walking of the subject to a predetermined number of steps starting at a time the subject starts walking, and the second data indicating a sway amount of the body of the subject during walking in a second walking section in a double task state in which the subject is walking while doing a given assignment, the second walking section being after the first walking section;
determining that the second walking section starts when the predetermined number of steps have passed from the starting of the first walking section;
obtaining a physical strength measurement data of the subject using at least one of a dynamic balance ability and an agility of the subject;
calculating, from the gait data obtained in the obtaining, a feature value that is based on the gait data and a motor feature value indicating a motor function of the subject using the physical strength measurement data;
evaluating a cognitive function and a motor function of subject based on the feature value and motor feature value of subject;
outputting evaluation results of the motor function and the cognitive function of the subject,
wherein obtaining the at least one of first data and second data includes obtaining the at least one of the first data and the second data each indicating, as the sway amount, a change amount of a displacement, a speed, or an acceleration of the subject during walking, and
calculating the feature value includes calculating a frequency spectrum by performing frequency analysis on the change amount of the displacement of the subject during walking, the change amount of the speed of the subject during walking, or the change amount of the acceleration of the subject during walking; and
calculating the feature value, based on an integral at a specific frequency higher than a frequency corresponding to walking in the frequency spectrum calculated, the specific frequency being 3 Hz or more, and
wherein degrees of cognitive function and motor function of the subject are determined, based on the feature value and motor feature value; and
displaying an image that notifies the subject of the evaluation results of the motor function and cognitive function of the subject, wherein
the image includes a motor function evaluation result notification portion and a cognitive function evaluation result notification portion,
the motor function evaluation result notification portion notifies the subject of the evaluation of the motor function of the subject, the motor function evaluation result notification portion including an evaluation result of the motor function of the subject and a comment based on the evaluation result being displayed on a same screen,
the cognitive function evaluation result notification portion notifies the subject of the evaluation of the cognitive function of the subject, the cognitive function evaluation result notification portion including an evaluation result of the motor function of the subject by evaluation unit and a comment based on the evaluation result, and
the motor function evaluation result notification portion and the cognitive function evaluation result notification portion being displayed simultaneously on a same screen.

14. A non-transitory computer-readable recording medium having recorded thereon a program for causing a computer to execute the cognitive function evaluation method according to claim 13.

* * * * *